(12) United States Patent
Fujinami et al.

(10) Patent No.: US 8,765,837 B2
(45) Date of Patent: Jul. 1, 2014

(54) DENTAL CURABLE COMPOSITION

(75) Inventors: Kyoichi Fujinami, Tsukuba (JP); Ayumi Dodomi, Tsukuba (JP); Koji Matsushige, Tsukuba (JP); Kazuhiko Okishio, Tsukuba (JP)

(73) Assignee: Tokuyama Dental Corporation, Tokyo (JP)

( * ) Notice: Subject to any disclaimer, the term of this patent is extended or adjusted under 35 U.S.C. 154(b) by 157 days.

(21) Appl. No.: 12/742,524

(22) PCT Filed: Nov. 14, 2008

(86) PCT No.: PCT/JP2008/070743
§ 371 (c)(1),
(2), (4) Date: May 12, 2010

(87) PCT Pub. No.: WO2009/063967
PCT Pub. Date: May 22, 2009

(65) Prior Publication Data
US 2010/0261144 A1 Oct. 14, 2010

(30) Foreign Application Priority Data
Nov. 15, 2007 (JP) ................................. 2007-297049

(51) Int. Cl.
*A61K 31/121* (2006.01)
*C08J 3/28* (2006.01)

(52) U.S. Cl.
USPC ........... 523/118; 523/115; 523/116; 522/184; 502/202

(58) Field of Classification Search
None
See application file for complete search history.

(56) References Cited

U.S. PATENT DOCUMENTS

| | | | | |
|---|---|---|---|---|
| 4,259,075 A * | 3/1981 | Yamauchi et al. | ......... | 433/217.1 |
| 4,259,117 A * | 3/1981 | Yamauchi et al. | ............... | 106/35 |
| 4,368,043 A * | 1/1983 | Yamauchi et al. | ............... | 523/118 |
| 4,539,382 A * | 9/1985 | Omura et al. | ................ | 526/276 |
| 4,612,384 A | 9/1986 | Omura et al. | | |
| 4,650,847 A | 3/1987 | Omura et al. | | |
| 5,260,476 A * | 11/1993 | Ohno et al. | ...................... | 560/90 |
| 5,530,038 A * | 6/1996 | Yamamoto et al. | ........... | 523/116 |
| 5,587,406 A * | 12/1996 | Yamamoto et al. | ........... | 523/116 |
| 5,744,511 A | 4/1998 | Kazama et al. | | |
| 5,866,631 A * | 2/1999 | Nakagawa et al. | ........... | 523/118 |
| 6,217,644 B1 * | 4/2001 | Matsunae et al. | ............... | 106/35 |
| 6,583,197 B1 * | 6/2003 | Wada et al. | ...................... | 522/84 |
| 6,759,449 B2 * | 7/2004 | Kimura et al. | ................ | 523/118 |
| 7,084,182 B2 * | 8/2006 | Hara et al. | ...................... | 522/14 |
| 7,488,762 B2 | 2/2009 | Takano et al. | | |
| 2003/0050359 A1 * | 3/2003 | Kimura et al. | ................ | 522/182 |
| 2004/0110864 A1 * | 6/2004 | Hecht et al. | .................... | 523/113 |
| 2004/0180983 A1 * | 9/2004 | Hara et al. | ...................... | 522/33 |
| 2005/0009946 A1 * | 1/2005 | Oguri et al. | .................... | 522/184 |
| 2006/0004122 A1 * | 1/2006 | Hecht et al. | .................... | 523/115 |
| 2006/0247328 A1 * | 11/2006 | Nakata et al. | ................. | 523/109 |
| 2007/0072957 A1 | 3/2007 | Noguchi et al. | | |
| 2007/0123605 A1 * | 5/2007 | Liu et al. | ....................... | 523/116 |

FOREIGN PATENT DOCUMENTS

| | | |
|---|---|---|
| JP | 52-113089 A | 9/1977 |
| JP | 53-113843 A | 10/1978 |
| JP | 58-021687 A | 2/1983 |
| JP | 4-214708 A | 8/1992 |
| JP | 09-309811 A | 2/1997 |
| JP | 9-227325 A | 9/1997 |
| JP | 10-236912 A | 9/1998 |
| JP | 2000-086421 A | 3/2000 |
| JP | 2001-072523 A | 3/2001 |
| JP | 2001-122718 A | 5/2001 |
| JP | 3388670 B2 | 1/2003 |
| JP | 2003-096122 A | 4/2003 |
| JP | 2004-529946 A | 9/2004 |
| JP | 2006-299201 A | 11/2006 |
| JP | 2007-091607 A | 4/2007 |
| WO | WO 03/027153 A1 | 4/2003 |

OTHER PUBLICATIONS

International Search Report for PCT/JP2008/070743, mailed Feb. 17, 2009.

* cited by examiner

*Primary Examiner* — James J. Seidleck
*Assistant Examiner* — Peter A Salamon
(74) *Attorney, Agent, or Firm* — Buchanan Ingersoll & Rooney PC

(57) ABSTRACT

[Problems] To provide a chemical polymerization type curable composition which can achieve a very large strength of adhesion even without irradiated with light, and is used in the field of dental therapy.
[Means for Solution] A dental curable composition comprising (A) a polymerizable monomer component containing an acidic group-containing polymerizable monomer, (B) water, and (C) a chemical polymerization initiator component comprising a radical-generating species and a reactive species that generates radicals upon reacting with the radical-generating species; wherein, the dental curable composition is stored being divided into a plurality of packages, and is polymerized and cured by mixing together the components contained in the packages; and wherein one package (I) among the packages contains the component (A) and the component (B), and, further, contains polyvalent metal ions in an amount of 0.3 to 10 meq per gram of the polymerizable monomer component (A) contained in the package; and the chemical polymerization initiator (C) is stored being divided into at least two packages so that the radical-generating species and the reactive species do not come in contact with each other.

13 Claims, No Drawings

DENTAL CURABLE COMPOSITION

TECHNICAL FIELD

This invention relates to a dental curable composition used in the field of dental therapy and, particularly, to a dental curable composition that can be favorably used as a dental adhesive.

BACKGROUND ART

Means for restoring a tooth that is damaged by, for example, decaying, generally, varies depending upon the degree of damage to the tooth. In the initial to middle stage of decaying, for example, a cavity formed in the tooth is relatively small. In this case, a direct restoration is employed, in many cases, to directly fill the cavity with a curable restorative from such standpoints that the restoring work can be done easily and quickly, and that the restored portion exhibits excellent aesthetic appearance. If the degree of damage is large and a relatively large cavity is formed in the tooth, an indirect restoration is employed, in many cases, to join a prosthetic material (comprising, for example, a metal, ceramics or resin) to the portion of the tooth that is to be restored, the prosthetic material having been prepared in advance outside of the oral cavity.

Here, the restorative such as a composite resin or a prosthetic material has no adhesiveness to the tooth. To adhere it to the tooth, therefore, use is made of a dental adhesive comprising a curable composition that contains a polymerizable monomer component and a polymerization initiator component. In such a dental adhesive, a (meth)acrylate type monomer is used as a chief component of the polymerizable monomer, a photopolymerization initiator is used as a polymerization initiator, and a cured body is, usually, formed by the radical polymerization upon being irradiated with light.

However, there have also been known dental adhesives comprising curable compositions containing a chemical polymerization initiator (see, for example, patent documents 1 to 8). For example, even if it is attempted to directly restore a greatly damaged tooth with its crown destroyed by using a curable restorative, i.e., even if the portion to be restored is irradiated with intense light, light fails to reach the bottom portions thereof to a sufficient degree. In this case, therefore, there is used an adhesive that contains a chemical polymerization initiator as described above. Further, if the indirect restoration is carried out by using a prosthetic material that does not permit the transmission of light, such as a metallic prosthetic material, the adhesive cannot be sufficiently cured by photopolymerization, either. In this case, too, therefore, there is used an adhesive containing a chemical polymerization type polymerization initiator. Namely, the chemical polymerization initiator contains a radical-generating species and a reactive species, and generates radicals which serve as polymerization-initiating species upon contacting these two components together. Therefore, the adhesive containing the chemical polymerization initiator undergoes the polymerization to form a cured body without the need of being irradiated with light.

Further, there have been developed adhesives containing a photopolymerization initiator as well as an acidic group-containing polymerizable monomer having adhesiveness to teeth in order to obtain a higher adhering strength (see, for example, patent documents 1 and 2). That is, acidic groups such as phosphoric acid group and carboxylic acid group have a high affinity to the teeth (hydroxyapatite or collagen). By using a polymerizable monomer having such an acidic group, a cured product can be formed that is highly adhesive to the teeth. Upon making present water together therewith, further, the adhesive containing the acidic group-containing polymerizable monomer exhibits both the demineralizing function (etching capability) and the penetrating function to the teeth owing to the action of the acidic group. Upon being applied only once, the adhesive adheres highly to the teeth even without using primer and can, therefore, be used as a one-step type adhesive offering excellent operability (see, for example, patent documents 4, 9 and 10).

There have, further, been proposed dental adhesives blended with a polyvalent metal ion-eluting filler in addition to being blended with the acidic group-containing polymerizable monomer and water (see, for example, patent documents 4 to 12). Here, the polyvalent metal ion-eluting filler stands for a filler that elutes out ions of a polyvalent metal such as an alkaline earth metal or aluminum in an acidic solution such as a fluoroaluminosilicate glass. With the above adhesives, polyvalent metal ions eluted out from the polyvalent metal ion-eluting filler at the time of curing ionically bond to the acidic groups of the acidic group-containing polymerizable monomer to form ionic crosslinking. Namely, the polymerizable monomer is polymerized while the ionic crosslinking is being formed contributing to greatly increasing the strength of the cured body that is obtained and, as a result, to further increasing the strength of adhesion to the teeth.

With the above adhesives, however, ionic crosslinking occurs excessively during the storage to form a gel. Therefore, the polyvalent metal ion-eluting filler is stored in a package separate from a package that contains the acidic group-containing polymerizable monomer and water. Just before the use, the components contained in the packages are mixed together and used.

There has, further, been proposed a dental adhesive using, as the acidic group-containing polymerizable monomer, a polymerizable monomer that contains a phosphoric acid group, the polymerizable monomer being blended in the form of a salt such as calcium salt. It has been reported that this adhesive exhibits excellent strength of adhesion to the teeth (patent document 3).

The above conventional means for improving adhesion are chiefly applied to the dental adhesives of the photopolymerization type containing photopolymerization initiators. If these means are applied to the adhesives of the chemical polymerization type that contain chemical polymerization initiators and that undergo polymerization and curing without being irradiated with light, however, satisfactory adhesion is not obtained. That is, according to the study conducted by the present inventors, the chemical polymerization type adhesive containing, for example, the acidic group-containing polymerizable monomer and the polyvalent metal ion-eluting filler exhibits a considerably large strength of adhesion in the initial stage of polymerization and curing. After the passage of a predetermined period of time in a severe environment in an oral cavity, however, the strength of adhesion decreases sharply and, therefore, it becomes very highly probable that the composite resin or the prosthetic material peels off.

Patent document 1: JP-A-52-113089
Patent document 2: JP-A-58-21687
Patent document 3: JP-A-53-113843
Patent document 4: JP-A-2001-72523
Patent document 5: JP-A-2006-299201
Patent document 6: Leaflet of International Publication WO03/027153
Patent document 7: JP-A-2007-91607
Patent document 8: JP-A-2001-122718

Patent document 9: JP-A-9-309811
Patent document 10: JP-A-2004-529946
Patent document 11: JP-A-10-236912
Patent document 12: JP-A-2000-86421

DISCLOSURE OF THE INVENTION

Problems that the Invention is to Solve

It is, therefore, an object of the invention to provide a dental curable composition of the chemical polymerization type containing a chemical polymerization initiator, which excels in adhering property to the teeth and in durability, and is capable of forming a cured body that exhibits a large strength of adhesion in the oral cavity comparable to that of in the initial stage even after stored for extended periods of time.

Means for Solving the Problems

The present inventors have conducted keen study concerning dental curable compositions containing a chemical polymerization initiator, have discovered the fact that when it is attempted to improve the adhering property of the cured body by forming ionic crosslinking relying upon polyvalent metal ions at the time of polymerization and curing, it is made possible not only to further greatly improve the adhering property but also to improve the durability of adhesion upon contriving the form of packaging and, therefore, to stably maintain excellent adhering property even in a severe environment in the oral cavity, and have completed the present invention.

According to the present invention, there is provided a dental curable composition including:
(A) a polymerizable monomer component containing an acidic group-containing polymerizable monomer;
(B) water; and
(C) a chemical polymerization initiator component comprising a radical-generating species and a reactive species that generates radicals upon reacting with the radical-generating species; wherein,
the dental curable composition is stored being divided into a plurality of packages, and is polymerized and cured by mixing together components contained in the packages; and wherein,
one package (I) among the packages contains the component (A) and the component (B), and, further, contains polyvalent metal ions in an amount of 0.3 to 10 meq per gram of the polymerizable monomer component (A) contained in the package; and
the chemical polymerization initiator (C) is stored being divided into at least two packages so that the radical-generating species and the reactive species do not come in contact with each other.

According to the present invention, further, there is provided a dental adhesive comprising the above curable composition.

Effects of the Invention

The dental curable composition of the invention exhibits improved curing property due to the ionic crosslinking introduced into the acidic group-containing polymerizable monomer (hereinafter often simply called acidic monomer) in the polymerizable monomer component (A) in addition to the curing by polymerization due to a chemical polymerization initiator. Therefore, a polymerized and cured body having a large strength is obtained.

Besides, what is important is that the invention employs such a packaging form that the acidic monomer necessary for forming ionic crosslinking, water and polyvalent metal ions are stored in the same package (I). Namely, owing to this packaging form, it is allowed to form the ionic crosslinking developed to a high degree. As a result, the effect for improving the curing property by ionic crosslinking is enhanced to a maximum degree and, therefore, the obtained cured body exhibits excellent adhering property to the teeth and, at the same time, exhibits excellent durability of adhesion. Even when held in a severe environment of oral cavity for extended periods of time, therefore, the cured body stably maintains a high level of strength of adhesion to the tooth, composite resin and prosthetic material.

In the case of a conventional dental adhesive that forms ionic crosslinking by using a polyvalent metal ion-eluting filler, for example, the filler which is the source of polyvalent ions is stored in a package separate from a package of storing the acidic monomer and water. Therefore, polyvalent metal ions generate after the filler has come in contact with the acidic aqueous solution by mixing the components in these packages together to use the adhesive. That is, the system that uses a chemical polymerization initiator initiates the polymerization without the need of being irradiated with light; i.e., the reaction of polymerization and curing readily takes place immediately after the components are mixed together. Namely, the time in which polyvalent metal ions elute out from the filler is very short. As a result, the ionic crosslinking does not sufficiently develop at the time of polymerization and curing and, therefore, the obtained cured body fails to have a sufficiently large strength accounting for insufficient effect for improving adhesion and very low durability of adhesion.

According to the present invention, on the other hand, the acidic monomer, water and polyvalent metal ions while being stored are in a state of being present together in the same package (I). At the time of using the adhesive by mixing the components together, therefore, the ionic crosslinking to be introduced into the acidic monomer has been developed to a sufficient degree. Despite the polymerization and curing take place immediately after a moment the components are mixed together, therefore, the effect for enhancing the curing property by ionic crosslinking can be attained to a maximum degree, and the strength of the cured body can be greatly increased.

Therefore, the dental curable composition of the invention capable of forming a cured body of a large strength as described above, makes it possible to strongly adhere the tooth to a dental restorative such as composite resin or prosthetic material even if it is the dentin or the enamel. Besides, the dental curable composition of the invention maintains a large strength of adhesion in the oral cavity for extended periods of time, and is capable of stably holding the restorative. The curable composition of the invention can be very advantageously used as a dental adhesive particularly when a greatly damaged tooth such as having its crown destroyed is directly restored by using a curable restorative, or when it is used where the photopolymerization cannot be applied such as when a tooth is indirectly restored by using a prosthetic such as a metal prosthetic that does not permit the transmission of light.

BEST MODE FOR CARRYING OUT THE INVENTION

The dental curable composition of the present invention contains, as basic components, (A) a polymerizable monomer component, (B) water, and (C) a chemical polymerization initiator component, which are stored being divided into a plurality of packages. Here, one package (I) among the plurality of packages contains the above components (A) and (B), and in which the polyvalent metal ions are adjusted to be present at a predetermined concentration. Further, the chemical polymerization initiator component (C) contains a radical-generating species and a reactive species. Here, however, the radical-generating species and the reactive species are stored being divided into separate packages so that the polymerization will not take place during the storage. When the components in the packages are mixed together at the time of use, the polymerization and curing take place due to the chemical polymerization. As required, further, the dental curable composition of the invention uses any other components. For example, a polyvalent metal ion source (D) is used to adjust the polyvalent metal ion concentration in the package (I) to lie in a predetermined range, an inorganic filler (E) is suitably used to increase the strength of the cured body, a volatile and water-soluble organic solvent (F) is used to improve the storage stability and, besides, any other various blending agents can be used in ranges in which they do not impair the object of the invention.

In the present invention, there is no limitation on the total number of packages for storing the dental curable composition so far as some components of the dental curable composition are stored in the package (I) so as to satisfy the above conditions and the chemical polymerization initiator component (C) is stored in a divided manner. Storing the dental curable composition in unnecessarily large number of packages, however, makes the mixing operation cumbersome at the time of use and, besides, causes such an inconvenience as an increased space for preserving the packages. Usually, therefore, the components in the packages are so adjusted that the number of packages can be settled to be 2 or 3, or, most desirably, 2.

The components used for the dental curable composition of the invention will now be described by taking the packaging form into consideration.

<(A) Polymerizable Monomer Components>

In the present invention, the polymerizable monomer component (A) (hereinafter simply referred to as "monomer component") is a basic component which is radically polymerizable, and is cured upon being polymerized with a polymerization initiator species (radical) generated by a chemical polymerization initiator that will be described later to form a cured body having a highly adhering property to the tooth such as enamel or dentin and to the restorative such as composite resin or prosthetic material (particularly, metallic material).

In order to realize demineralizing property (etching power) to the tooth (particularly, to the enamel) and penetration into the tooth (particularly, into the dentin), it is desired that not less than 5% by mass of the monomer component (A) is an acidic group-containing polymer (acidic monomer) (a1). That is, if the amount of the acidic monomer (a1) is small, the curable composition fails to exhibit sufficiently large etching power to the tooth. It, therefore, becomes necessary to pretreat the tooth to secure a sufficiently large strength of adhesion to the tooth.

The monomer component (A) may all be the acidic group-containing polymer (a1). From the standpoint of maintaining a balance in the strength of adhesion to both the enamel and the dentin and improving water-resisting property and durability of adhesion yet maintaining excellent strength of adhesion of the cured body in the oral cavity, however, it is desired that the monomer component (A), further, contains a polymerizable monomer (a2) without having acidic group.

Desirably, for example, the content of the acidic group-containing polymer (a1) in the monomer component (A) is in a range of 5 to 80% by mass and, particularly, 15 to 60% by mass, and the remainder is the polymerizable monomer (a2) without containing acidic group. Here, if the content of the acidic monomer (a1) is small, the strength of adhesion to the enamel tends to decrease and if the content thereof is large, on the other hand, the strength of adhesion to the dentin tends to decrease.

Acidic Group-Containing Polymerizable Monomers (a1):

In the present invention, there is no particular limitation on the acidic group-containing polymerizable monomer, i.e., on the acidic monomer (a1) provided it is a compound having at least one acidic group and at least one polymerizable unsaturated group in a molecule thereof, and any known compound can be used.

Described below are examples of the acidic group which the acidic monomer (a1) has in its molecules.

Examples of Acidic Group:

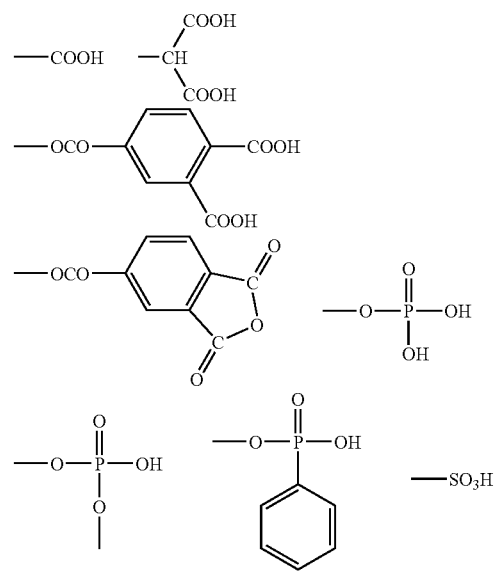

Among the above acidic groups according to the present invention, it is most desired to use phosphoric acid type groups, such as —O—P(=O)(OH)$_2$ and (—O—)$_2$P(=O)OH. When the acidic monomer having such an acidic group is used, a high demineralizing action is exhibited to the tooth (probably due to that the group of the phosphoric acid type has a strong acidity) and, besides, a large bonding force to the tooth is obtained making it possible to attain a particularly large strength of adhesion.

Further, as the polymerizable unsaturated group which the acidic monomer (a1) has in its molecules, there can be exemplified acryloyl group, methacryloyl group, acrylamide group, methacrylamide group, vinyl group, allyl group, ethenyl group and styryl group.

In the present invention, concrete examples of the acidic monomer (a1) having the above acidic group and the polymerizable unsaturated group in its molecules are represented by the following compounds Representative examples of the acidic group-containing polymerizable monomer (a1):
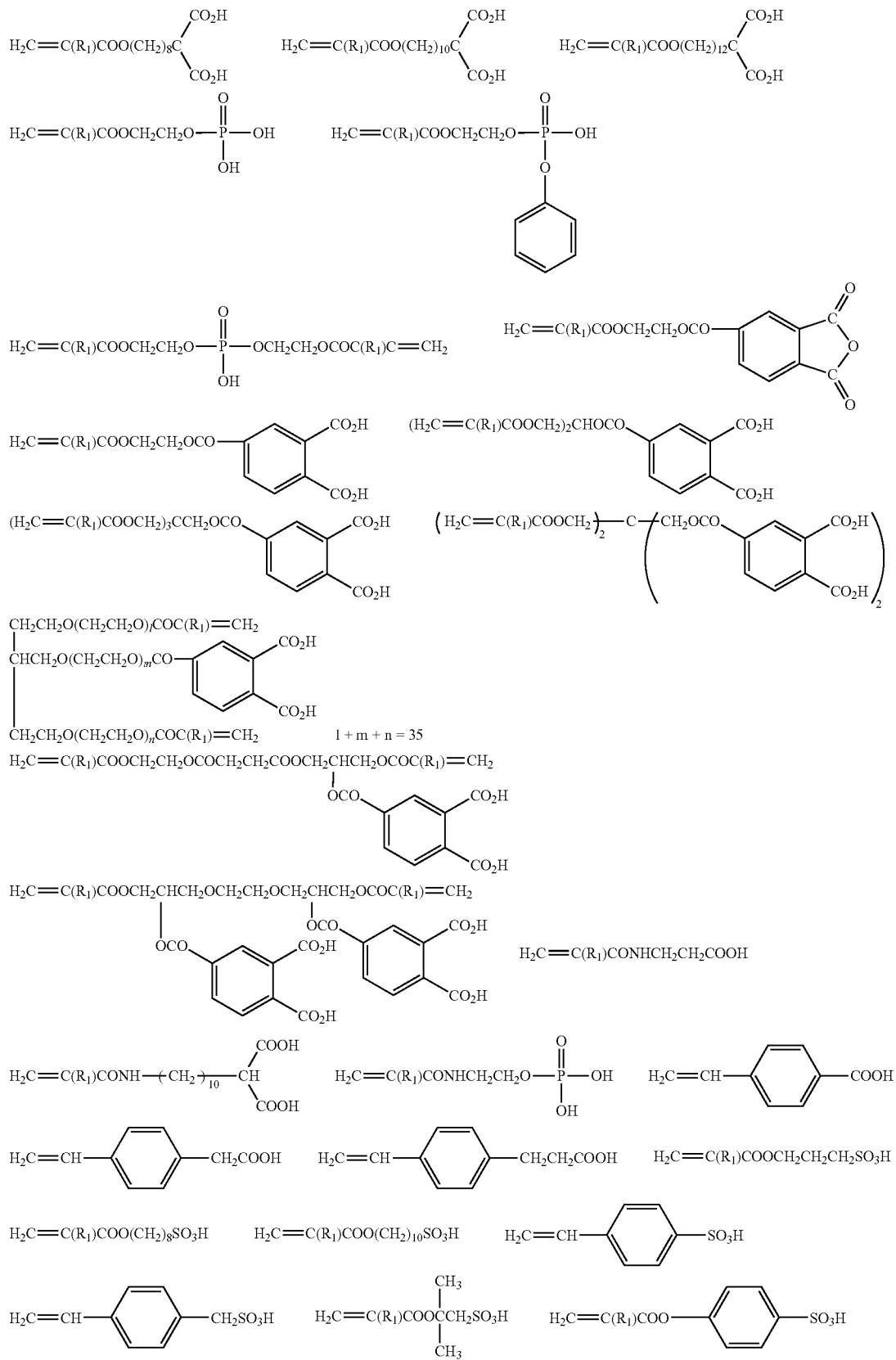

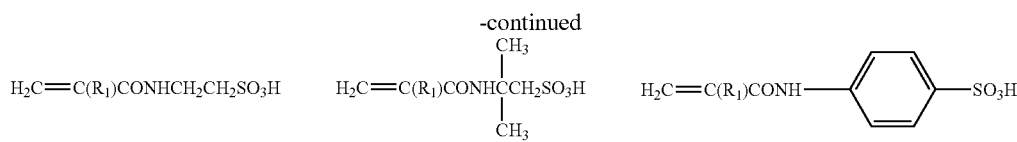

wherein $R^1$ is a hydrogen atom or a methyl group.

In addition to the above compounds, there can be used, as the acidic monomer (a1), vinylphosphonic acids in which a phosphonic acid group is directly bonded to a vinyl group, acrylic acid, methacrylic acid and vinylsulfonic acid.

The acidic monomers (a1) exemplified above can be used alone or being mixed together in two or more kinds. Among them, it is desired to use a compound (polybasic acid monomer) in which the acid has a valency of two or more in the molecules thereof from the standpoint of enhancing the ionic bond to the polyvalent metal ions that will be described later and obtaining a strong adhesion. The polybasic acid monomer may have two or more monovalent acid groups in the molecules or may have at least one acid group having a valency of two or more in the molecules.

Use of the polybasic acid monomer only as the acidic monomer (a1) is desirable from the standpoint of improving the strength of adhesion causing, however, a slight decrease in the storage stability. It is, therefore, desired that the polybasic acid monomer is used in combination with a compound that has a monovalent acid in the molecules. In this case, the polybasic acid monomer and the compound (monovalent monomer) having a monovalent acid are most desirably those having the above phosphoric acid type group. It is, further, desired that the ratio (molar ratio) of the amount of the compound (monovalent monomer) having a monovalent acid and the amount of the polybasic acid monomer having an acid of a valency of two or more is in a range of, polybasic acid monomer/monovalent monomer=0.3 to 2

In this system, not only a high demineralizing action is obtained for the tooth but also a substantially large bonding force to the tooth is attained and, a particularly large strength of adhesion is obtained offering favorable storage stability.

From the standpoint of curing rate, further, it is desired that the acidic monomer (a1) is a compound having acryloyl group, methacryloyl group, acrylamide group or methacrylamide group as a polymerizable unsaturated group.

Depending upon the kind of the chemical polymerization initiator component (C) that will be described later, further, the above acidic monomer (a1) also works as a reactive species in the component (C).

Polymerizable Monomers without Acidic Group (a2):

As the polymerizable monomer (a2) without acidic group that can be used together with the acidic monomer (a1), i.e., as the non-acidic monomer, there can be used any known compound without any limitation so far as the compound satisfies the condition that it has no acidic group but has at least one polymerizable unsaturated group in the molecules. As the polymerizable unsaturated groups possessed by the polymerizable monomer, there can be exemplified those exemplified concerning the above acidic monomer (a1) and, particularly preferably, acryloyl group, methacryloyl group, acrylamide group and methacrylamide group.

The above non-acidic monomer (a2) can be represented by the following (meth)acrylate type monomers which can be used alone or in a combination of two or more kinds.

1. Mono(meth)acrylate type monomers:
methyl(meth)acrylate,
ethyl(meth)acrylate,
glycidyl(meth)acrylate,
2-cyanomethyl(meth)acrylate,
benzyl(meth)acrylate,
polyethylene glycol mono(meth)acrylate,
allyl(meth)acrylate,
2-hydroxyethyl(meth)acrylate,
glycidyl(meth)acrylate,
3-hydroxypropyl(meth)acrylate,
glycerylmono(meth)acrylate,
2-(meth)acryloxyethylacetyl acetate, etc.
2. Polyfunctional (meth)acrylate type monomers:
ethylene glycol di(meth)acrylate,
diethylene glycol di(meth)acrylate,
triethylene glycol di(meth)acrylate,
nonaethylene glycol di(meth)acrylate,
propylene glycol di(meth)acrylate,
dipropylene glycol di(meth)acrylate,
2,2'-bis[4-(meth)acryloyloxyethoxyphenyl]propane,
2,2'-bis[4-(meth)acryloyloxyethoxyethoxyphenyl]propane,
2,2'-bis{4-[3-(meth)acryloyloxy-2-hydroxypropoxy] phenyl}propane,
1,4-butanediol di(meth)acrylate,
1,6-hexanediol di(meth)acrylate,
trimethylolpropane tri(meth)acrylate,
urethane(meth)acrylate,
epoxy(meth)acrylate, etc.

It is, further, allowable to use a polymerizable monomer other than the above (meth)acrylate type monomer. As the other polymerizable monomer, there can be exemplified fumaric acid ester compounds such as monomethyl fumarate, diethyl fumarate and diphenyl fumarate; styrene compounds such as styrene, divinylbenzene, α-methylstyrene and α-methylstyrene dimer; and allyl compounds such as diallyl phthalate, diallyl terephthalate, diallyl carbonate and allyl diglycol carbonate. These other polymerizable monomers can be used in one kind or in two or more kinds being mixed together.

In the invention, further, when a highly hydrophobic polymerizable monomer is used as the non-acidic monomer (a2), it is desired to use in combination an amphipatic monomer such as 2-hydroxyethyl(meth)acrylate or 2-hydroxypropyl (meth)acrylate. This is because use of the amphipatic monomer in combination makes it possible to prevent isolation of water which is an essential component of the curable composition of the invention, to maintain homogeneity of the composition and to obtain stable and large strength of adhesion.

Form of Packaging the Monomer Component (A)

In the present invention, the above monomer component (A) is stored in the same package (I) as the water (B) that will be described later. Here, the monomer component (A) may be partly stored in other packages. That is, upon containing part of the monomer component (A) in the other packages so as to increase the amount of the components contained in the other packages, the amount of the components contained in the other packages can be set to be of the same level as the amount of the components contained in the package (I) to facilitate the operation for mixing the components contained in the packages.

Further, when part of the monomer component (A) is stored in the other packages, it is desired that the monomer component (A) stored in the other packages is the non-acidic monomer (a2). Or, in other words, the acidic monomer (a1) is stored in the whole amount in the package (I), and the non-acidic monomer (a2) is at least partly stored in the other packages. That is, the acidic monomer (a1) reacts with other components to lower the functions of other components or to lower the ionic crosslinking. Therefore, limitation is imposed on the components that can be made present therewith. If the acidic monomer (a1) is stored being divided into a plurality of packages, therefore, the components that cannot be contained in the acidic monomer (a1)-containing packages must be contained in a further package inviting an inconvenience of an increase in the total number of packages. Therefore, it is desired that the acidic monomer (a1) is stored in the whole amount in the package (I) only while the non-acidic monomer (a2) is at least partly stored in the packages other than the package (I) to thereby adjust the amounts of components contained in the packages.

When the non-acidic monomer (a2) is at least partly stored in the other packages, there is no particular limitation on the amount of the non-acidic monomer (a2) stored in the other packages. Generally, however, the non-acidic monomer (2a) is stored in the other packages in an amount of not more than 2 mass times and, particularly, in a range of 0.1 to 2 mass times of the monomer component (A) stored in the package (I). In this case, the other packages for storing the non-acidic monomer (a2) may be of a number of one or of a plural number, and the amount of the non-acidic monomer (a2) contained in the packages other than the package (I) may be determined within the above range so that the amounts of the components contained in the packages are of the same level.

<(B) Water and Form of its Package>

Water which is the component (B) works as a solvent for homogeneously dispersing the components and is, at the same time, necessary for demineralizing the tooth and for accelerating the ionic crosslinking of the acidic monomer (a1) with polyvalent metal ions. Preferably, there is used such water as distilled water or deionized water substantially free of impurities detrimental to the storage stability and medicinal components.

The water is stored in the package (I) which contains the above acidic monomer (a1). The water, however, can also be contained in the other packages so far as water is contained in a predetermined amount in the package (I).

In the present invention, it is desired that water is stored in the package (I) in an amount in a range of 3 to 30 parts by mass, particularly, 5 to 20 parts by mass and, most desirably, 1.0 to 20 parts by mass per 100 parts by mass of the monomer component (A) stored in the package (I). If the amount of water that is added is smaller than the above range, it becomes probable that demineralization of the tooth and ionic crosslinking become insufficient, and the strength of adhesion may decrease. At the time of polymerization and curing, the water is removed by blowing the air thereto. If water is contained in the package (I) in an amount in excess of the above range, however, it becomes difficult to remove water at the time of polymerization and curing, and water remains much on the tooth surface making it difficult to obtain a sufficiently large adhering strength causing a decrease in the water-resisting property and in the durability of adhesion.

In case water is stored in the packages other than the package (I), too, use of water in large amounts makes it difficult to remove water at the time of polymerization and curing. It is therefore recommended to so determine the amount of water to be used that the total amount of water stored in the package (I) and in other packages (i.e., in the whole packages) is in a range of not larger than 30 parts by mass per 100 parts by mass of the total amount of the monomer component (A) in the whole packages.

<(C) Chemical Polymerization Initiator Components>

The chemical polymerization initiator which is the component (C) comprises a radical-generating species and a reactive species that generates radicals (polymerization-initiating species) upon reacting with the radical-generating species. There have been known a variety of kinds of chemical polymerization initiators. In the invention, the chemical polymerization initiator of any composition can be used. Representatively, however, there can be used the one of such a composition as aryl borate compound (radical-generating species)/acidic compound (reactive species), or organic peroxide (radical-generating species)/amine compound (reactive species). Most desirably, there is used a chemical polymerization initiator of the aryl borate type of which the activity is not decreased by the above acidic monomer (a1). This is because the chemical polymerization initiator which uses an organic peroxide as the radical-generating species permits the amine compound used as the reactive species to easily react with the acidic monomer (a1) bringing about a decrease in the activity.

As described above, the chemical polymerization initiator of the aryl borate type uses an aryl borate compound as the radical-generating species and uses an acidic compound as the reactive species. As required, further, the chemical polymerization initiator of the aryl borate type uses, as the radical generation accelerator, at least any one of those selected from metal compounds of valencies of +II to +V (particularly, a vanadium compound having a valency of +IV or +V) and an organic peroxide. That is, as represented by the following formula (1), it is considered that by using the chemical polymerization initiator of the aryl borate type, the aryl borate compound reacts with the acidic compound to form a triphenylborane, benzo radicals are generated from the formed triphenylborane, and the polymerization reaction is accelerated by the benzo radicals that work as an initiator. The above radical generation accelerator works to accelerate the generation of benzo radicals from the triphenylborane.

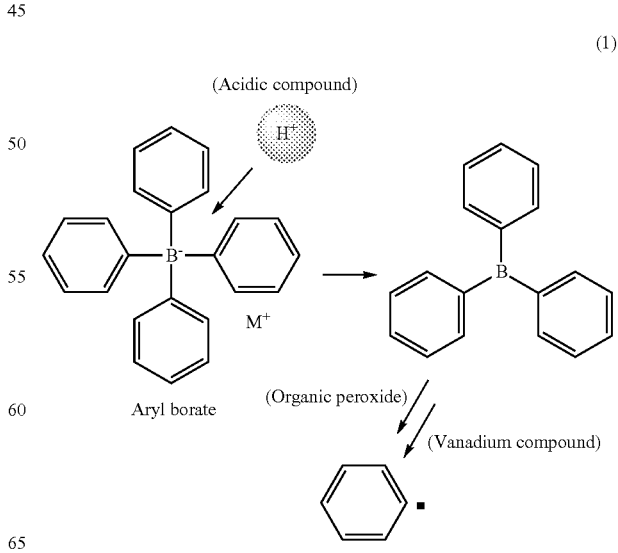

(1)

The aryl borate compound used as the radical-generating species has at least one boron-aryl bond in the molecules, and is concretely represented by the following formula (2).

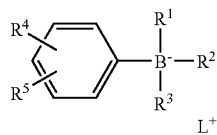

wherein $R^1$, $R^2$ and $R^3$ are, respectively, alkyl groups, aryl groups, aralkyl groups or alkenyl groups, $R^4$ and $R^5$ are, respectively, hydrogen atoms, halogen atoms, nitro groups, alkyl groups, alkoxy groups or phenyl groups, and $L^+$ is a metal cation, quaternary ammonium ion, quaternary pyridinium ion, quaternary quinolinium ion or phosphonium ion.

A borate compound without boron-aryl bond, too, can serve as a source of radicals. Because of its poor storage stability, however, this borate compound cannot, usually, be used as the source of radicals in the present invention. Namely, the borate compound without the boron-aryl bond easily decomposes upon reacting with oxygen in the air. Therefore, even, for example, in a packaged state, it easily deteriorates or readily undergoes the curing reaction at the time of being mixed or kneaded offering little time for charging the paste of the curable composition into the damaged portion of the tooth or for molding the paste of the curable composition into a predetermined shape, making it virtually difficult to use the curable composition. The aryl borate compound of the above formula (2), on the other hand, has a suitable degree of stability and does not cause the above problems.

In the formula (2) representing the structure of the aryl borate compound, the groups $R^1$ to $R^3$ are alkyl groups, aryl groups, aralkyl groups or alkenyl groups which may have a substituent.

Among these groups, the alkyl group may be either the one of a straight chain or a branched one. Though there is no particular limitation, the alkyl group is, desirably, the one having 3 to 30 carbon atoms and, more desirably, the straight-chain alkyl group having 4 to 20 carbon atoms, such as n-butyl group, n-octyl group, n-dodecyl group or n-hexadecyl group. As the substituent which may be possessed by the alkyl group, there can be exemplified a halogen atom such as fluorine atom, chlorine atom or bromine atom, a hydroxyl group, nitro group or cyano group, or an aryl group having 6 to 10 carbon atoms, such as phenyl group, nitrophenyl group or chlorophenyl group, an alkoxy group having 1 to 5 carbon atoms, such as methoxy group, ethoxy group or propoxy group, or an acyl group having 2 to 5 carbon atoms, such as acetyl group. There is no particular limitation, either, on the number and position of the substituent.

There is no particular limitation on the aryl group which, therefore, may have a substituent. Desirably, the aryl group has 6 to 14 carbon atoms (excluding carbon atoms possessed by the substituent) with which a single ring or 2 or 3 rings are condensed. As the substituent which the aryl group may have, there can be exemplified the groups that were exemplified as the substituents for the above alkyl group, as well as alkyl groups having 1 to 5 carbon atoms, such as methyl group, ethyl group and butyl group. Concrete examples of the aryl group are as described below.

phenyl group,
1- or 2-naphthyl group,
1-, 2- or 9-anthryl group,
1-, 2-, 3-, 4- or 9-phenanthryl group,
p-fluorophenyl group,
p-chlorophenyl group,
(3,5-bistrifluoromethyl)phenyl group,
3,5-bis(1,1,1,3,3,3-hexafluoro-2-methoxy-2-propyl)phenyl group,
p-nitrophenyl group,
m-nitrophenyl group,
p-butylphenyl group,
m-butylphenyl group,
p-butyloxyphenyl group,
m-butyloxyphenyl group,
p-octyloxyphenyl group,
m-octyloxyphenyl group, etc.

There is no particular limitation on the aralkyl group which, therefore, may have a substituent. Generally, there can be exemplified those having 7 to 20 carbon atoms (excluding carbon atoms possessed by substituent), such as benzyl group, phenetyl group or tolyl group. As the substituent, further, there can be exemplified those substituents that were exemplified for the above aryl group.

There is no particular limitation on the alkenyl group which, therefore, may have a substituent. Preferably, there can be used an alkenyl group having 4 to 20 carbon atoms (excluding carbon atoms possessed by the substituent), such as 3-hexenyl group or 7-octenyl group. As the substituent, further, there can be exemplified those substituents that were exemplified for the above alkyl group.

In the above general formula (2), $R^4$ and $R^5$ are, respectively, hydrogen atoms, halogen atoms, nitro groups, alkyl groups, alkoxy groups or phenyl groups.

There is no particular limitation on the alkyl groups or alkoxy groups represented by $R^4$ and $R^5$, which, therefore, may be of a straight chain or a branched chain and may, further, have a substituent. Preferably, however, these groups have 1 to 10 carbon atoms (excluding carbon atoms of the substituent). As the substituent, further, there can be exemplified those substituents for the alkyl groups represented by $R^1$ to $R^3$ above. Concrete examples of such alkyl groups include methyl group, ethyl group, n- or i-propyl group, n-, i- or t-butyl group, chloromethyl group, trifluoromethyl group, methoxymethyl group, and 1,1,1,3,3,3-hexafluoro-2-methoxy-2-propyl group. As the alkoxy group, there can be exemplified methoxy group, ethoxy group, 1- or 2-propoxy group, 1- or 2-butoxy group, 1-, 2- or 3-octyloxy group and chloromethoxy group.

Further, the phenyl groups represented by $R^4$ and $R^5$ may have a substituent. As the substituent, there can be exemplified those substituents for the aryl groups represented by $R^1$ to $R^3$ above.

In the above general formula (2), further, $L^+$ is a metal cation, tertiary or quaternary ammonium ion, quaternary pyridinium ion, quaternary quinolinium ion or quaternary phosphonium ion.

As the metal cations, there can be preferably used alkali metal cations such as sodium ions, lithium ions or potassium ions, or alkaline earth metal cations such as magnesium ions and as the tertiary or quaternary ammonium ions, there can be exemplified tetrabutylammonium ions, tetramethylammonium ions, tetraethylammonium ions, tributylammonium ions, and triethanolammonium ions. The quaternary pyridinium ions can be represented by methylquinolinium ions, ethylquinolinium ions and butylquinolinium ions. As the quaternary phosphonium ions, further, there can be exemplified tetrabutylphosphonium ions and methyltriphenylphosphonium ions.

In the present invention, preferred examples of the aryl borate compound represented by the above formula (2) are those having an aryl group in a molecule thereof, those having two aryl groups in a molecule thereof, those having three aryl groups in a molecule thereof and those having four aryl groups in a molecule thereof.

The following boron compound salts are concrete examples of the aryl borate compound having an aryl group in a molecule thereof.

Examples of Boron Compound:
trialkylphenylboron,
trialkyl(p-chlorophenyl)boron,
trialkyl(p-fluorophenyl)boron,
trialkyl(3,5-bistrifluoromethyl)phenylboron,
trialkyl[3,5-bis(1,1,1,3,3,3-hexafluoro-2-methoxy-2-propyl)phenyl]boron,
trialkyl(p-nitrophenyl)boron,
trialkyl(m-nitrophenyl)boron,
trialkyl(p-butylphenyl)boron,
trialkyl(m-butylphenyl)boron,
trialkyl(p-butyloxyphenyl)boron,
trialkyl(m-butyloxyphenyl)boron,
trialkyl(p-octyloxyphenyl)boron,
trialkyl(m-octyloxyphenyl)boron, etc.
(the alkyl group is n-butyl group, n-octyl group, n-dodecyl group, etc.)

As the salt of the boron compound, there can be exemplified sodium salt, lithium salt, potassium salt, magnesium salt, tetrabutylammonium salt, tetramethylammonium salt, tetraethylammonium salt, tributylamine salt, triethanolamine saltl, methylpyridinium salt, ethylpyridinium salt, butylpyridinium salt, methylquinolinium salt, ethylquinolinium salt and butylquinolinium salt.

The following boron compound salts are concrete examples of the aryl borate compound having two aryl groups in a molecule thereof.

Examples of Boron Compound:
dialkyldiphenylboron,
dialkyldi(p-chlorophenyl)boron,
dialkyldi(p-fluorophenyl)boron,
dialkyldi(3,5-bistrifluoromethyl)phenylboron,
dialkyldi[3,5-bis(1,1,1,3,3,3-hexafluoro-2-methoxy-2-propyl)phenyl]boron,
dialkyl(p-nitrophenyl)boron,
dialkyldi(m-nitrophenyl)boron,
dialkyldi(p-butylphenyl)boron,
dialkyldi(m-butylphenyl)boron,
dialkyldi(p-butyloxyphenyl)boron,
dialkyldi(m-butyloxyphenyl)boron,
dialkyldi(p-octyloxyphenyl)boron,
dialkyldi(m-octyloxyphenyl)boron, etc.
(the alkyl group is n-butyl group, n-octyl group, n-dodecyl group, etc.)

As the salts thereof, further, there can be exemplified those compounds exemplified for the aryl borate compound having an aryl group in a molecule thereof.

The following boron compound salts are concrete examples of the aryl borate compound having three aryl groups in a molecule thereof.

Examples of Boron Compound:
monoalkyltriphenylboron,
monoalkyltris(p-chlorophenyl)boron,
monoalkyltris(p-fluorophenyl)boron,
monoalkyltris(3,5-bistrifluoromethyl)phenylboron,
monoalkyltris[3,5-bis(1,1,1,3,3,3-hexafluoro-2-methoxy-2-propyl)phenyl]boron,
monoalkyltris(p-nitrophenyl)boron,
monoalkyltris(m-nitrophenyl)boron,
monoalkyltris(p-butylphenyl)boron,
monoalkyltris(m-butylphenyl)boron,
monoalkyltris(p-butyloxyphenyl)boron,
monoalkyltris(m-butyloxyphenyl)boron,
monoalkyltris(p-octyloxyphenyl)boron,
monoalkyltris(m-octyloxyphenyl)boron, etc.
(the alkyl group is n-butyl group, n-octyl group, n-dodecyl group, etc.)

As the salts thereof, further, there can be exemplified those compounds exemplified for the aryl borate compound having an aryl group in a molecule thereof.

The following boron compound salts are concrete examples of the aryl borate compound having four aryl groups in a molecule thereof.

Examples of Boron Compound:
tetraphenylboron,
tetrakis(p-chlorophenyl)boron,
tetrakis(p-fluorophenyl)boron,
tetrakis(3,5-bistrifluoromethyl)phenylboron,
tetrakis[3,5-bis(1,1,1,3,3,3-hexafluoro-2-methoxy-2-propyl)phenyl]boron,
tetrakis(p-nitrophenyl)boron,
tetrakis(m-nitrophenyl)boron,
tetrakis(p-butylphenyl)boron,
tetrakis(m-butylphenyl)boron,
tetrakis(p-butyloxyphenyl)boron,
tetrakis(m-butyloxyphenyl)boron,
tetrakis(p-octyloxyphenyl)boron,
tetrakis(m-octyloxyphenyl)boron, etc.
(the alkyl group is n-butyl group, n-octyl group, n-dodecyl group, etc.)

As the salts thereof, further, there can be exemplified those compounds exemplified for the aryl borate compound having an aryl group in a molecule thereof.

In the present invention, it is desired to use an aryl borate compound having three or four aryl groups in a molecule thereof from the standpoint of storage stability. However, the aryl borate compound having four aryl groups is most desired from the standpoint of further improved storage stability, easy handling and easy availability. The above aryl borate compounds can be used in one kind or in two or more kinds being mixed together.

The aryl borate compound which is the above radical-generating species is, usually, used in an amount of 0.01 to 10 parts by mass and, particularly, 0.1 to 8 parts by mass per 100 parts by mass of the monomer component (A) (i.e., the whole amount of the monomer component (A) contained in the packages) used in the curable composition.

In the aryl borate type chemical polymerization initiator, further, the oxidizing compound used as the reactive species serves as a proton source which reacts with the aryl borate compound to form an arylborane which generates benzo radicals that serve as a polymerization-initiating species.

Though the above acidic monomer (a1) represents the above acidic compound, it is also allowable to use those inorganic acids and organic acids that have, usually, been known as Bromsted acids as the oxidizing compounds that work as reactive species.

Typical examples of the inorganic acid include hydrochloric acid, sulfuric acid, nitric acid and phosphoric acid. Representative examples of the organic acid include carboxylic acids such as acetic acid, propionic acid, maleic acid, fumaric acid, phthalic acid, benzoic acid, trichloroacetic aid, trifluoroacetic acid, citric acid and trimellitic acid; sulfonic acids such as p-toluenesulfonic acid, benzenesulfonic acid, methanesulfonic acid and trifluoromethanesulfonic acid; and phosphoric acids such as methylphosphonic acid, phenylphosphonic acid, dimethylphosphinic acid and diphenylphosphinic acid.

In addition to phenols and thiols, it is further allowable to use such solid acids as acidic ion-exchange resin and acidic alumina as acidic compounds that serve as reactive species.

It is desired that the acidic compound that serves as the reactive species is, usually, used in an amount of 0.1 to 100 mols and, particularly, 0.5 to 50 mols per mol of the above aryl borate compound. Therefore, if the amount of the acidic monomer (a1) that is used is in the above range, there is no need of using any other acidic compound. If the amount is not in the above range, however, it is desired to use the above organic acid or inorganic acid as the acidic compound to adjust the amount of the acidic compound inclusive of the acidic monomer (a1) so as to lie in the above range. When the acidic monomer (a1) is used in large amounts, further, it is desired to adjust the amount of the aryl borate compound that is used so that the amount of the acidic compound (acidic monomer (a1)) lies in the above range.

Further, the metal compound having a valency of +II to +V used as the radical generation accelerator works to accelerate the decomposition of arylborane such as triphenylborane formed by the reaction of the aryl borate compound with the acidic compound, enabling benzo radicals to be quickly formed.

As the metal compound, there can be used, for example, vanadium compound, iron compound, copper compound, molybdenum compound, manganese compound, cobalt compound, tungsten compound or tin compound without any particular limitation. Among them, however, it is desired to use a vanadium compound having a valency of +IV or +V.

Described below are concrete examples of the vanadium compound which may be used alone or in two or more kinds in combination.
divanadium tetroxide (IV),
vanadium oxide acetylacetonato (IV),
vanadyl oxalate (IV),
vanadyl sulfate (IV),
oxobis(1-phenyl-1,3-butanedionate)vanadium (IV),
bis(maltolato)oxovanadium (IV),
vanadium pentoxide (V),
sodium metavanadate (V),
ammon metavanadate (V), etc.

The above metal compound is, usually, used in an amount of 0.001 to 10 parts by mass and, particularly, 0.01 to 1 part by mass per 100 parts by mass of the whole amount of the monomer component (A) used in the curable composition.

As the radical generation accelerator for the aryl borate type chemical polymerization initiator, further, an organic peroxide can be used. When the organic peroxide is used in combination with the above vanadium compound, in particular, generation of benzo radicals can be most effectively accelerated.

Representative examples of the organic peroxide that can be used in the invention include various organic peroxides that can be classified into ketone peroxide, peroxyketal, hydroperoxide, diaryl peroxide, peroxy ester, diacyl peroxide and peroxy dicarbonate. Described below are concrete examples of these organic peroxides.
Ketone Peroxides:
methyl ethyl ketone peroxide,
cyclohexanone peroxide,
methylcyclohexanone peroxide,
methylacetoacetate peroxide,
acetylacetone peroxide, etc.
Peroxyketals:
1,1-bis(t-hexylperoxy)3,3,5-trimethylcyclohexane,
1,1-bis(t-hexylperoxy)cyclohexane,
1,1-bis(t-butylperoxy)3,3,5-trimethylcyclohexane,
1,1-bis(t-butylperoxy)cyclohexane,
1,1-bis(t-butylperoxy)cyclododecane,
2,2-bis(t-butylperoxy)butane,
n-buty 4,4-bis(t-butylperoxy)valerate,
2,2-bis(4,4-di-t-butylperoxycyclohexyl)propane, etc.
Hydroperoxides:
P-menthane hydroperoxide,
diisopropylbenzene hydroperoxide,
1,1,3,3-tetramethylbutyl hydroperoxide,
cumene hydroperoxide,
t-hexyl hydroperoxide,
t-butyl hydroperoxide, etc.
Dialky peroxides:
α,α-bis(t-butylperoxy)diisopropylbenzene,
dicumyl peroxide,
2,5-dimethyl-2,5-bis(t-butylperoxy)hexane,
t-butylcumyl peroxide,
di-t-butyl peroxide,
2,5-dimethyl-2,5-bis(t-butylperoxy)hexyne-3, etc.
Diacyl Peroxides:
isobutyl peroxide,
2,4-dichlorobenzoyl peroxide,
3,5,5-trimethylhexanoyl peroxide,
octanoyl peroxide,
lauroyl peroxide,
stearyl peroxide,
succinic acid peroxide,
m-toluoylbenzoyl peroxide,
benzoyl peroxide, etc.
Peroxy Dicarbonates:
di-n-propylperoxy dicarbonate,
diisopropylperoy dicarbonate,
bis(4-t-butylcyclohexyl)peroxy dicarbonate,
di-2-ethoxyethylperoxy dicarbonate,
di-2-ethylhexylperoxy dicarbonate,
di-2-methoxybutylperoxy dicarbonate,
di(3-methyl-3-methoxybutyl)peroxy dicarbonate, etc.
Peroxy Esters:
α,α-bis(neodecanoylperoxy)diisopropylbenzene,
cumylperoxy neodecanoate,
1,1,3,3-tetramethylbutylperoxy neodecanoate,
1-cyclohexyl-1-methylethylperoxy neodecanoate,
t-hexylperoxy neodecanoate,
t-butylperoxy neodecanoate,
t-hexylperoxy pivalate,
t-butylperoxy pivalate,
1,1,3,3-tetramethylbutylperoxy-2-ethyl hexanoate,
2,5-dimethyl-2,5-bis(2-ethylhexanoylperoxy)hexane,
1-cyclohexyl-1-methylethylperoxy-2-ethy hexanoate,
t-hexylperoxy 2-ethyl hexanoate,
t-butylperoxy 2-ethy hexanoate,
t-butylperoxyiso butylate,
t-hexylperoxyisopropyl monocarbonate,
t-butylperoxymaleic acid,
t-butylperoxy 3,5,5-trimethyl hexanoate,
t-butylperoxy laurate,
2,5-dimethyl-2,5-bis(m-toluoylperoxy)hexane,
t-butylperoxyisopropyl monocarbonate,
t-butylperoxy 2-ethylhexyl monocarbonate,
t-hexylperoxy benzoate,
2,5-dimethyl-2,5-bis(benzoylperoxy)hexane, t-butylperoxy acetate,
t-butylperoxy-m-toluoyl benzoate,
t-butylperoxy benzoate,
bis(t-butylperoxy)isophthalate, etc.

In addition to the above organic peroxides, there can be preferably used t-butyltrimethylsilyl peroxide, 3,3',4,4'-tetra (t-butylperoxycarbonyl)benzophenone and the like.

Among the above organic peroxides, the present invention desirably uses ketone peroxides, peroxy esters or diacyl peroxides and, most desirably uses diacyl peroxides or hydroperoxides from the standpoint of polymerizing activity.

The above organic peroxides are usually used in an amount of 0.01 to 10 parts by mass and, particularly, 0.1 to 8 parts by mass per 100 parts by mass of the whole amount of the monomer component (A) used in the curable composition.

It is, further, most desired that the organic peroxides are used in combination with the above metal compound as described above.

In the chemical polymerization initiator that uses the organic peroxide as the radical-generating species, an amine compound is used as the reactive species. This system uses the organic peroxides which are the same as those exemplified above. The organic peroxides in this system, however generate radicals by themselves but do not exhibit the above-mentioned radical generation acceleration function. In this system, further, there is used a primary amine, a secondary amine or a tertiary amine as the amine compound. Preferably, however, there is used the tertiary amine having a particularly high activity, e.g., such toluidines as N,N-dimethyl-p-toluidine, N,N-diethyl-p-toludine or N,N-di(hydroxyalkyl)-p-toluidine.

In the above organic peroxide type chemical polymerization initiator component, it is desired that the organic peroxide is used in an amount of 0.1 to 10 parts by mass and, particularly, 0.5 to 5 parts by mass per 100 parts by mass of the whole amount of the monomer component (A) used in the curable composition and that the amine compound is used in an amount of 0.05 to 5 parts by mass and, particularly, 0.1 to 3 parts by mass per 100 parts by mass of the whole amount of the monomer component (A) used in the curable composition.

Form of Packaging the Chemical Polymerization Initiator Component (C)

In the present invention, it is important that the above chemical polymerization initiator component (C) is stored being divided into the radical-generating species and the reactive species or, in other words, stored being divided into separate packages. That is, if the radical-generating species and the reactive species are made present together, radicals which are the polymerization-initiating species are generated during the storage causing gelation to take place during the storage, or the generated radicals are dissipated and no polymerization initiating function is exhibited at the time of use.

A concrete form of packaging the chemical polymerization initiator component (C) is determined depending upon the kind thereof in a manner that the properties will not be lost and that a favorable storage stability is attained.

When, for example, the aryl borate type chemical polymerization initiator is used, the aryl borate compound which is the radical-generating species is stored in a package different from the package (I) mentioned above. That is, the acidic monomer (a1) that is stored in the package (I) works as the reactive species. Therefore, if the aryl borate compound is stored in the package (I), then radicals generate during the storage in the package (I) and, therefore, gelation takes place.

If an acidic compound other than the acidic monomer (a1) is used as the reactive species in the system, then the acidic compound is stored in the package (I).

In the aryl borate type chemical polymerization initiator, further, the metal compound such as vanadium compound used as the radical generation accelerator may be stored in either package. Usually, however, the metal compound is desirably stored in the package (I) that contains the acidic monomer (a1). This is because in the package (I), the concentration of polyvalent metal ions is adjusted to lie in a predetermined range to form ionic crosslinking, the above metal compound also works as a source of polyvalent metal ions and, besides, the metal compound is further stabilized due to the ionic crosslinking.

The organic peroxide used together with the above metal compound as the radical generation accelerator, on the other hand, is stored in a package separate from the package (I) that contains the acidic monomer (a1). This is because the organic peroxide has a low storage stability under acidic conditions.

If the organic peroxide type chemical polymerization initiator is used, the organic peroxide which is the radical-generating species is stored in the package separate from the package (I) on account of the same reason as above. Here, further, the amine compound which is the reactive species, too, is stored in the package separate from the package (I). This is because if the amine compound is stored in the package (I), the ionic crosslinking is lost due to the neutralization of the amine compound with the acidic monomer (a1) and, besides, the radical-generating capability may be lost due to the neutralization. If the organic peroxide type chemical polymerization initiator is used, therefore, it becomes necessary to use a package (II) for storing the organic peroxide and a package (III) for storing the amine compound in addition to the package (I); i.e., at least three packages must be used.

<(D) Polyvalent Metal Ion Sources>

In the package (I) which contains water and the monomer component (A) that includes the acidic monomer (a1) according to the present invention, the concentration of polyvalent metal ions is so adjusted as to be 0.3 to 10.0 meq per gram of the monomer component (A) in the package (I). That is, upon adjusting the concentration of polyvalent metal ions to lie in the above range, the ionic crosslinking is formed to a sufficient degree in the package (I) during the storage. When the components in the packages are mixed together so as to be put to use, therefore, the chemical polymerization starts taking place immediately. In this case, however, the ionic crosslinking has been formed already to a sufficient degree, which makes it possible to form a cured body having a large strength maintaining excellent adhering property and durability of adhesion. For example, if the concentration of polyvalent metal ions is lower than the above range (0.3 meq), the ionic crosslinking becomes insufficient and the strength of adhesion to the tooth decreases. If the concentration thereof is higher than the above range (10 meq), on the other hand, the tooth-demineralizing power by the acidic monomer (a1) may decrease. From the standpoint of forming the ionic crosslinking to a more sufficient degree and forming the cured body having a particularly large strength, therefore, the concentration of polyvalent metal ions is so adjusted as to lie, preferably, from 1.0 to 10.0 meq, more preferably, from 1.0 to 7.0 meq and, most preferably, from 1.5 to 6.8 meq per gram of the monomer component (A) in the package (I).

As the concentration of polyvalent metal ions increases, however, gelation tends to take place easily in the package (I). Therefore, the concentration of polyvalent metal ions is adjusted to be, preferably, from 0.4 to 6.0 meq and, most preferably, from 0.6 to 3.0 meq per gram of the monomer component (A) in the package (I) from the standpoint of forming the cured body having a favorable strength and giving importance to the storage stability over extended periods of time.

To find the concentration of polyvalent metal ions, the concentrations of various kinds of ions are measured by the ICP (inductively coupled plasma) emission spectroscopy or the atomic absorption spectroscopy, and the amount of ionic bond of polyvalent metal ions to the monomer component (A) is converted into a milliequivalent per gram of the monomer component (A) relying on the measured values. Therefore, the concentration of polyvalent metal ions can be found as the sum of values obtained by multiplying the concentrations of various kinds of polyvalent metal ions (mmol/g) per gram of the monomer component (A) by the valencies of the respective kinds of metal ions.

To adjust the concentration of polyvalent metal ions in the package (I) to lie in the above range as described above, the polyvalent metal ion source (D) is added into the package (I). Metal compounds such as vanadium compound, etc. described above can serve as the polyvalent metal ion sources. Usually, however, the concentration of polyvalent metal ions fails to lie in the above range and, therefore, a separate source of polyvalent metal ions becomes necessary.

The polyvalent metal ions stand for metal ions having a valency of two or more which can be bonded to acidic groups possessed by the acidic monomer (a1), and any polyvalent ions can be used so far as they are capable of being bonded to the acidic groups. From the standpoint of dental use, however, it is desired to use ions of lanthanoid such as calcium, strontium, barium, aluminum, scandium, titanium, zinc, magnesium, zirconium, vanadium, chromium, manganese, iron, cobalt, nickel, copper, lanthanum and ytterbium. Among them, ions having a valency of three or more are desired from the standpoint of high adhering property. Most desirably, therefore, aluminum ions, lanthanum ions or titanium ions are contained as a component from the standpoint of safety to the living body in addition to high adhering property.

As the ion source for making polyvalent metal ions present in the package (I) at the above high concentration according to the present invention, it is allowable to use such ionic compounds as alkoxides, water-soluble salts, water-soluble hydroxides, water-soluble oxides or complex salts of the above polyvalent metals in amounts depending upon their solubilities or dissociations. Though not limited thereto only, described below are concrete examples of the polyvalent metal sources.

Polyvalent Metal Alkoxides:
aluminum triisopropoxide,
magnesium hydroxide,
calcium hydroxide,
barium hydroxide,
lanthanum triisopropoxide,
scandium triisopropoxide,
ytterbium triisopropoxide,
chromium triisopropoxide,
titanium tetraisopropoxide,
zirconium tetraisopropoxide,
iron (III) ethoxide,
copper (II) ethoxide,
zinc bis(2-methoxyethoxide).
Water-Soluble Salts of Polyvalent Metals:
aluminum salicylate,
aluminum chloride.
Water-Soluble Hydroxides of Polyvalent Metals:
aluminum hydroxide,
calcium hydroxide,
lanthanum hydroxide,
magnesium hydroxide,
barium hydroxide.
Water-Soluble Oxides of Polyvalent Metals:
aluminum oxide.
Complex salts of polyvalent metals:
vanadium (III) tetrakisacetyl acetonato,
manganese (III) tetrakisacetyl acetonato,
cobalt (III) tetrakisacetyl acetonato,
nickel (II) tetrakisacetyl acetonato.

In the invention, further, it is also allowable to use polyvalent metal ion-eluting fillers (hereinafter simply referred to as polyvalent metal fillers) as the sources of polyvalent metal ions in addition to the above polyvalent metal compounds. That is, the polyvalent metal filler has a function for improving the mechanical strength of the cured body and offers an advantage of improving, particularly, the durability of the cured body.

The polyvalent metal filler may contain monovalent metal ions such as of sodium so far as it is capable of eluting out the polyvalent metal ions in the above range. However, the monovalent metal ions that are contained in too large amounts affect the ionic crosslinking by the polyvalent metal ions. It is, therefore, desired that the monovalent metal ions are contained in amounts as small as possible. Usually, it is desired that the content of monovalent metal ions in the polyvalent metal filler is not more than 10 mol % and, particularly, not more than 5 mol % of the content of polyvalent metal ions.

Elution of polyvalent metal ions from the polyvalent metal filler is, usually, completed in about 3 hours to about 12 hours at room temperature (23° C.) after the preparation of the tooth surface coating material. When the polyvalent metal filler is used, therefore, the amount of polyvalent metal ions is substantially equal to the amount of polyvalent metal ions 24 hours after the preparation at room temperature (23° C.), and can be calculated from the total amount of polyvalent metal ions contained in the polyvalent metal filler and the amount of the monomer component (A) in the package (I).

There is no particular limitation on the polyvalent metal filler provided it is capable of eluting out polyvalent metal ions in an amount in the above-mentioned range. If the polyvalent metal ions are contained in the form of a salt capable of eluting out counter anions simultaneously with the polyvalent metal ions, however, then the eluted and dissociated counter anions may adversely affect the strength of adhesion (this also holds when a water-soluble salt of a polyvalent metal is used). In the present invention, therefore, it is desired to use a polyvalent metal filler that does not elute out counter anions simultaneously with the polyvalent metal ions. As the polyvalent metal filler that satisfies the above condition, there can be exemplified glasses having a skeleton of a chain-like, lamellar or mesh-like structure containing polyvalent metal ions in the gaps of the skeleton.

As the glasses, there can be preferably used those containing oxide glass components, such as aluminosilicate glass, borosilicate glass and soda-lime glass, as well as those containing fluoride glass components, such as zirconium fluoride glass. Namely, after having eluted out the polyvalent metal ions, the polyvalent metal filler comprising glasses containing the above components assumes the form of porous particles having a mesh-like structure that exhibit the action for improving the mechanical strength of the cured body formed from the curable composition and for improving the strength of the layer for adhesion.

Among the above polyvalent metal fillers according to the present invention, it is desired to use the aluminosilicate glass from the standpoint of strength of the cured body and it is most desired to use the fluoroaluminosilicate glass which gradually releases fluorine and gradually releases, from the cured body, fluoride ions that work to reinforce the teeth.

Polyvalent metal ion elution characteristics of the polyvalent metal filler can be controlled depending on the blending ratio of various elements contained in the filler. For example, if the contents of polyvalent metal ions such as aluminum, calcium, etc. increase, the amounts of elution thereof, usually, increase. Upon varying the contents of sodium and phosphorus, further, the amounts of elution of polyvalent metal ions can be varied. Thus, the polyvalent metal ion elution properties can be controlled relatively easily.

The polyvalent metal filler elution properties can also be controlled relying on a generally known method. As a representative method, there has been known a method in which polyvalent metal ions on the surfaces of the polyvalent metal filler are removed in advance by treating the filler with an acid to thereby control the elution properties. This method uses a generally known acid which may be an inorganic acid like hydrochloric acid or nitric acid, or an organic acid like maleic acid, organosulfonic acid or citric acid. The concentration of acid and treating time may be suitably determined depending upon the amount of ions to be removed.

As the fluoroaluminosilicate glass preferred as the polyvalent metal filler, further, there can be used a known one used, for example, for a dental glass ionomer cement. The fluoroaluminosilicate glass that is widely known has the following composition as expressed by ionic mass percent.

silicon; 10 to 33%, particularly, 15 to 25%
aluminum; 4 to 30%, particularly, 7 to 20%
alkaline earth metal; 5 to 36%, particularly, 8 to 28%
alkali metal; 0 to 10%, particularly, 0 to 10%
phosphorus; 0.2 to 16%, particularly, 0.5 to 8%
fluorine; 2 to 40%, particularly, 4 to 40%
oxygen; balance As the alkaline earth metal, further, calcium is generally used. It is, further, desired that calcium is partly or wholly replaced by magnesium, strontium or barium. Most generally, further, sodium is used as the alkali metal, and it is, further, desired that sodium is partly or wholly replaced by lithium or potassium. As required, further, it is allowable to use, as a polyvalent metal filler, a glass in which aluminum is partly or wholly replaced by metal ions having a valency of three or more, such as of titanium, yttrium, zirconium, hafnium, tantalum or lanthanum.

The particles of the polyvalent metal filler may have any shape without limitation, such as pulverized shape as obtained by an ordinary pulverization or spherical shape which, as required, may be mixed with particles of a plate-like shape or fibrous shape.

It is, further, desired that the polyvalent metal filler has an average particle diameter ($D_{50}$), as measured by, for example, a laser diffraction/scattering method and calculated as a volume, in a range of 0.01 μm to 5 μm, particularly, 0.05 μm to 3 μm, and, most desirably, 0.1 μm to 2 μm from the standpoint of being homogeneously dispersed in the curable composition. From the standpoint of easily adjusting the amount of elution of polyvalent metal ions to lie in the above range, further, it is desired that when 0.1 g of the filler is dipped and held in 10 ml of an aqueous solution containing 10% by weight of maleic acid at a temperature of 23° C. for 24 hours, the amount of elution of polyvalent metal ions is 5.0 to 500 meq/g of filler and, particularly, 10 to 100 meq/g of filler. In this case, too, the amount of polyvalent metal ions can be measured relying on the ICP emission spectroscopy or the atomic absorption spectroscopy. The amount of elution of polyvalent metal ions after 24 hours have passed under the above conditions is hereinafter also called "amount of ion elution in 24 hours".

If the above polyvalent metal filler is used as a source of polyvalent metal ions, the storage stability may often be lowered due to the sedimentation of filler components. Therefore, upon making a predetermined amount of polyvalent metal ions present in the package (I) by using the polyvalent metal filler to maintain a predetermined polyvalent metal ion concentration, the filler from which the polyvalent metal ions have been eluted out can be removed by filtering. In this case, it is desired that the polyvalent metal filler has an average particle diameter ($D_{50}$), as measured by, for example, the laser diffraction/scattering method and calculated as a volume, in a range of 1 μm to 200 μm, particularly, 3 μm to 50 μM and, most desirably, 5 μm to 40 μm from the standpoint of easy removal.

<(E) Inorganic Fillers that Elute No Polyvalent Metal Ion>

In the invention, an inorganic filler can be used to improve the strength of the cured body that is formed. The inorganic filler is not used for eluting polyvalent metal ions and is, therefore, clearly distinguished from the above polyvalent metal ion-eluting filler since it is not to elute out polyvalent metal ions. The inorganic filler is a component that is desirably used when the curable composition of the invention is used as an adhesive for adhering and fixing, to the tooth, the composite resin that is used for the direct restoration or when the curable composition of the invention is used as the composite resin itself.

The inorganic filler can be stored in any package. As the inorganic filler, there can be exemplified inorganic particles comprising such metal oxides as quartz, silica, silica-alumina, silica-titania, silica-zirconia, silica-magnesia, silica-calcia, silica-barium oxide, silica-strontium oxide, silica-titania-sodium oxide, silica-titania-potassium oxide, titania, zirconia and alumina.

Among the above inorganic fillers, there can be preferably used inorganic fillers comprising metal oxide particles such as of silica, alumina or zirconia, or comprising composite metal oxide particles such as of silica-titania or silica-zirconia. There is no particular limitation either on the particle diameter or shape of these fillers like the fillers for general dental compositions.

Further, if the dental curable composition of the invention is used as an adhesive for adhering the composite resin that is used for direct restoration or is used as the composite resin itself, then it is desired to use a fumed silica as the inorganic filler.

The fumed silica is an amorphous silica produced by the frame hydrolytic method and, concretely, is produced by subjecting the silicon tetrachloride to the high-temperature hydrolysis in oxyhydrogen flame and, usually, has an average primary particle diameter of about 5 to about 100 nm, preferably, about 5 to about 20 nm, and has a mild tertiary aggregated structure.

As the fumed silica, there can be used a conventionally known one without any limitation, desirably, having a BET specific surface area of not less than 70 $m^2/g$ and, more preferably, 100 to 300 $m^2/g$.

Upon being imparted with hydrophobic property by using a surface-treating agent as represented by the silane coupling agent, the inorganic filler exhibits improved affinity to the polymerizable monomer component (A) and works to improve mechanical strength and water-resisting property.

Though not limited thereto only, described below are examples of the silane coupling agent used for imparting phydrophobic property.

Silane Coupling Agents:
methyltrimethoxysilane,
methyltriethoxysilane,
methyltrichlorosilane,
dimethyldichlorosilane,
trimethylchlorosilane,
vinyltrimethoxysilane,
vinyltriethoxysilane,
vinyltrichlorosilane,
vinyltriacetoxysilane,
vinyltris(β-methoxyethoxy)silane,
γ-methacryloyloxypropyltrimethoxysilane,
γ-methacryloyloxypropyltris(β-methoxyethoxy)silane,
γ-chloropropyltrimethoxysilane,
γ-chloropropylmethyldimethoxysilane,
γ-glycidoxypropyltrimethoxysilane,
γ-glycidoxypropylmethyldiethoxysilane,
β-(3,4-epoxycyclohexyl)ethyltrimethoxysilane,
N-phenyl-γ-aminopropyltrimethoxysilane, and
hexamethyldisilazane.

In addition to the treatment for imparting hydrophobic property by using the silane coupling agent, there are a method that uses titanate type coupling agent, aluminate type coupling agent or zirconate-aluminate type coupling agent, and a method that graft-polymerizes a polymerizable monomer on the surfaces of inorganic filler particles.

Though there is no particular limitation, it is desired that the treatment for imparting hydrophobic property is, generally, executed, in the case of the fumed silica, to such a degree that an M-value representing the oleophilic property is not less than 40 and, more preferably, 45 to 55. This enhances the dispersion of the inorganic filler such as fumed silica making it possible to effectively prevent the sedimentation and separation in the package for storage. Here, the M-value is a parameter measured by utilizing the fact that the silica floats on water but completely sinks in methanol. Namely, the larger this value, the stronger the hydrophobic property. The M-value is measured by a method described in Examples appearing later.

The inorganic filler is stored in any package being mixed together with other components and its amount can be suitably determined depending upon the use. For example, if the curable composition of the invention is used as an adhesive for direct restoration, the inorganic filler is used, preferably, in an amount of 0.5 to 100 parts by mass and, particularly, 5 to 40 parts by mass per 100 parts by mass of the whole amount of the monomer component (A). If the curable composition is used as the composite resin, the inorganic filler is used, preferably, in an amount of 50 to 1000 parts by mass and, particularly, 200 to 900 parts by mass per 100 parts by mass of the whole amount of the monomer component (A). Further, if the curable composition is used as the adhesive for indirect restoration, such as for adhering a metal prosthetic, the inorganic filler is used, preferably, in an amount of 50 to 1000 parts by mass and, particularly, 100 to 400 parts by mass per 100 parts by mass of the whole amount of the monomer component (A).

<(F) Volatile Water-Soluble Organic Solvents>

In order to improve penetrating property of the curable composition of the invention and, further, to improve storage stability of the components contained in the packages, a volatile water-soluble organic solvent is used. The organic solvent is useful particularly when the curable composition of the invention is used in the form of a liquid composition of a low viscosity (e.g., when used as an adhesive for a direct restorative).

Here, the volatility stands for that a boiling point under 760 mmHg is not higher than 100° C. and a vapor pressure at 20° C. is not less than 1.0 Kpa. Further, the water-solubility stands for that the solubility in water at 20° C. is not less than 20 g/100 ml.

It is, further, desired that the organic solvent (F) is blended in the package (I) together with, particularly, the monomer component (A), water (B) and polyvalent metal ion source (D). Namely, the concentration of polyvalent metal ions in the package (I) is diluted, gelation due to ionic crosslinking is effectively prevented, and storage is substantially improved.

In the invention, it is desired that the amount of the water-soluble organic solvent (F) blended in the package (I) satisfies a condition expressed by the following formula (3):

$$\alpha \geq 10 \cdot X \text{ (particularly, } 20 \cdot X, \text{ most desirably, } 25 \cdot X) \quad (3)$$

wherein α is the amount of the organic solvent (F) blended in the package (I) per 100 parts by mass of the monomer component (A), and X is the amount of polyvalent metal ions in the package (I) and is a number representing the amount (meq) per gram of the monomer component (A).

That is, if the blended amount of the organic solvent (F) is smaller than the above range, gelation may easily take place due to ionic crosslinking in the package (I). Namely, use of the organic solvent (F) in the above amount makes it possible to effectively prevent the gelation.

Further, the organic solvent (F) can be blended in other packages, too, to effectively prevent the sedimentation and separation of the components in other packages. Here, it is desired that the total amount of the organic solvent (F) used for the curable composition is in a range of 10 to 800 parts by mass and, particularly, 100 to 600 parts by mass per 100 parts by mass of the whole amount of the monomer component (A). That is, use of the organic solvent (F) in amounts in the above range enables the curable composition to highly penetrate into the tooth contributing to effectively improving the strength of adhering the cured body that is formed and improving the durability of adhesion. For example, if the organic solvent (F) is used an amount larger than the above range, it may become difficult to remove the organic solvent (F) when the curable composition is used whereby the concentration of the curable components becomes low at the time of curing, which may result in a decrease in the strength of adhering the obtained cured body, in the durability of adhesion and in the water-resisting property.

As the volatile water-soluble organic solvent, there can be exemplified methanol, ethanol, n-propanol, isopropyl alcohol, acetone and methyl ethyl ketone. As required, these organic solvents can be used in a plurality of kinds being mixed together. If toxicity to the living body is taken into consideration, it is desired to use ethanol, isopropyl alcohol and acetone.

<Other Blending Agents>

In the present invention, a variety of blending agents can be used in addition to the above components. For example, by using a photopolymerization initiator as required, the polymerization and curing can be executed by the irradiation with light, and the applicability can be expanded. When the photopolymerization initiator is blended, in particular, the time for polymerization and curing can be shortened by the irradiation with light even when the curing is conducted at a portion where little light reaches. Therefore, the curable composition of the invention can be advantageously used for the applications of, for example, building an abutment.

There can be used any known photopolymerization initiator without limitation. Concretely, there can be exemplified a compound which by itself undergoes the decomposition by the irradiation with light to form radical species and a system thereof to which a polymerization accelerator is added. The photopolymerization initiator can be stored being blended in any package so far as it remains stable. Depending upon the kind thereof, however, the photopolymerization initiator reacts with the acidic monomer (a1) causing a decrease in the activity. In such a case, the photopolymerization initiator is blended in a package separate from the package (I).

Though not limited thereto only, described below are examples of the compound which by itself undergoes the decomposition by the irradiation with light to form radical species.

α-Diketones:
camphorquinone,
benzyl,
α-naphthyl,
acetonaphthene,
naphthoquinone,
1,4-phenanthrenequinone,
3,4-phenanthrenequinone,
9,10-phenanthrenequinone.
Thioxanthones:
2,4-diethylthioxanthone.
α-Aminoacetophenones:
2-benzyl-dimethylamino-1-(4-morpholinophenyl)-butanone-1,
2-benzyl-diethylamino-1-(4-morpholinophenyl)-butanone-1,
2-benzyl-dimethylamino-1-(4-morpholinophenyl)-propanone-1,
2-benzyl-diethylamino-1-(4-morpholinophenyl)-propanone-1,
2-benzyl-dimethylamino-1-(4-morpholinophenyl)-pentanone-1,
2-benzyl-diethylamino-1-(4-morpholinophenyl)-pentanone-1.
Acylphosphinoxide derivatives:
2,4,6-trimethylbenzoyldiphenylphosphinoxide,
bis(2,6-dimethoxybenzoyl)-2,4,4-trimethylpentyl phosphinoxide.

Among the above compounds, α-aminoacetophenones, in particular, react with the acidic monomer (a1) to cause a decrease in the activity. Therefore, α-aminoacetophenones are blended in a package other than the package (I). In this case, further, to reliably prevent a decrease in the activity caused by the contact of the compound with the acidic monomer (a1) at the time of polymerization and curing, it is desired to use, as the acidic monomer (a1), a monomer that has a carboxylic acid as an acidic group when the α-aminoacetophenones are used.

As the polymerization accelerator, further, there can be used tertiary amines and, particularly, those tertiary amines having a weak acid-neutralizing action, such as 4-(N,N-dimethylamino)benzoic acid, lower alkyl (C1 to C4) esters of 4-(N,N-dimethylamino)benzoic acid and 4'-dimethylaminoacetophenone; barbituric acids such as 5-butylbarbituric acid and 1-benzyl-5-phenylbarbituric acid; and mercapto compounds such as dodecylmercaptane and pentaerythritoltetrakis(thioglycolate).

It is, further, desired to use not only the above photopolymerization initiator but also a photopolymerization initiator comprising coloring matter/photo acid generator/aryl borate compound, and those described in, for example, Japanese Patent No. 3449388 and Japanese Patent No. 3388670. In these photopolymerization initiators, the aryl borate compound is blended in a package other than the package (I) like in the case of the chemical polymerization initiator (C).

The amount of the photopolymerization initiator (inclusive of the polymerization accelerator) that is blended may be suitably determined without any particular limitation provided the amount is effective in curing the curable composition. Usually, however, it is desired to blend the photopolymerization initiator in an amount in a range of 0.01 to 5 parts by mass and, particularly, 0.1 to 2 parts by mass per 100 parts by mass of the whole amount of the monomer component (A).

As required, further, the dental curable composition of the present invention is blended with various additives such as organic viscosity-imparting agent, polymerization inhibitor, polymerization regulator, ultraviolet ray absorber, dye, pigment, perfume, antistatic agent and inorganic or organic acid in each of the packages. If blended in the package (I), attention should be so given that performance is not hindered by the acidic monomer (a1).

<Dental Curable Compositions>

The curable composition of the invention comprising the above components is stored being divided into a plurality of packages. At the time of use, the components stored in the packages are mixed together so as to be polymerized and cured to thereby form a cured body. In the package (I) which contains the acidic monomer (a1), water (B) and polyvalent metal ions, in particular, there have been formed acidic groups possessed by the acidic monomer (a1) and ionic crosslinking that has been developed. That is, the components in a state where the ionic crosslinking is sufficiently formed are mixed with the components of other packages, and the polymerization and curing take place due to the chemical polymerization. Therefore, despite the polymerization and curing quickly proceed after the mixing, the cured product becomes dense to a sufficient degree due to ionic crosslinking. Thus, there is formed the cured body having a large strength and a large durability of adhesion.

As required, further, the components to be contained in the packages are homogeneously mixed together by using a kneader under the illumination of inert light such as red light to prepare a liquid or paste-like mixture thereof which is then contained in predetermined packages. It is desired that the amounts of the components to be contained in the packages are so adjusted as to be of nearly the same level from the standpoint of easy mixing operation at the time of use. For instance, as compared to the amount of the components contained in the package (I), the amounts of components to be contained in other packages are 0.1 to 10 times, preferably, 0.2 to 4 times and, particularly preferably, of an equal amount irrespective of the number of the packages.

The curable composition of the invention prepared by taking out the components from the packages and mixing them together, is applied to a predetermined part depending on the use. Thereafter, water (B) and organic solvent (F) are removed from the composition by blowing the air thereto. Thus, the curable components are condensed, the polymerization and curing proceed quickly, and a cured body is formed having a large strength.

There is no particular limitation on the use of the dental curable composition of the invention provided it is used for the teeth. Concretely, the dental curable composition of the invention can be used as dental composite resin, dental adhesive, dental pre-treating material, lining material for the denture base, resin for the denture base, instantly polymerizing resin of the normal-temperature polymerization type, dental coating material and pit rill-plugging material, and is, preferably, used as the dental adhesive among such uses.

The dental adhesive can be favorably used as either an adhesive for direct restoration or an adhesive for indirect restoration. By utilizing the feature of curing by chemical polymerization, in particular, the dental adhesive can be effectively used in the case of directly restoring the tooth that is greatly damaged, such as breakage of the crown of a tooth by using a curable restorative (composite resin) or in the case of indirect restoration by using a metallic prosthetic that does not transmit light. The dental adhesive can be, further, effectively used as a pre-treating material in the case of using an adhesive for indirect restoration that requires pre-treatment, or can be, further, used as a composite resin or dental cement to serve as a direct restorative.

EXAMPLES

The invention will now be concretely described by way of Examples and Comparative Examples to which only, however, the invention is in no way limited. The kinds of components used in the following Examples and Comparative Examples, and the methods of testing and evaluating the properties were as described below.

<(A) Polymerizable Monomer Components>
[(a-1) Acidic Group-Containing Polymerizable Monomers (Acidic Monomers)]
 PM: A mixture of 2-methacryloyloxyethyldihydrogen phosphate and bis(2-methacryloyloxyethyl)hydrogen phosphate
 MDP: 10-Methacryloyloxydecyldihydrogen phosphate
 MAC-10: 11-Methacryloyloxy-1,1-undecanedicarboxylic acid The above acidic monomer (a-1) also works as a reactive species in the aryl borate type chemical polymerization initiator component.

[(a-2) Polymerizable Monomers without Acidic Group (Non-Acidic Monomers)]
 BisGMA: 2,2'-Bis[4-(2-hydroxy-3-methacryloxypropoxy)phenyl]propane
 3G: Triethylene glycol dimethacrylate
 HEMA: 2-Hydroxyethyl methacrylate <(C) Chemical Polymerization Type Polymerization Initiator Components>
 PhBTEOA: tetraphenyl borate triethanolamine salt
 BPO: benzoyl peroxide
 DEPT: N,N-dihydroxyethyl-p-toluidine
 POH: 1,1,3,3-tetramethylbutylhydroperoxide
 BMOV: bis(maltolato)oxovanadium (IV)

<(D) Polyvalent Metal Ion Sources>
[Polyvalent Metal Ion-Eluting Fillers (Polyvalent Metal Fillers)]
 F-1: Polyvalent metal filler obtained in Preparation Example 1,
  Average particle diameter: 0.5 μm,
  Amount of ions eluted out in 24 hours: 10 meq/g of filler
 F-2: Polyvalent metal filler obtained in Preparation Example 2,
  Average particle diameter: 0.5 μm,
  Amount of ions eluted out in 24 hours: 25 meq/g of filler
 F-3: Polyvalent metal filler obtained in Preparation Example 3,
  Average particle diameter: 0.5 μm,
  Amount of ions eluted out in 24 hours: 50 meq/g of filler <(E) Inorganic Fillers>
 FS1: Fumed silica (treated with methyltrichlorosilane),
  Average primary particle diameter; 18 nm
  BET specific surface area; 120 m$^2$/g
  M-value; 47
 FS2: Fumed silica (treated with dimethyldichlorosilane),
  Average primary particle diameter; 7 nm
  BET specific surface area; 230 m$^2$/g
  M-value; 52
 MS: Fused silica (treated with 3-methacryloxypropyltrimethoxysilane),
  Average primary particle diameter; 0.4 μm
  BET specific surface area; 8 m$^2$/g
 SS: Sol-gel silica (treated with 3-methacryloxypropyltrimethoxysilane),
  Average primary particle diameter; 60 nm
  BET specific surface area; 70 m$^2$/g
 GF: Amorphous silica-zirconia (treated with γ-methacryloxypropyltrimethoxysilane),
  Average particle diameter; 3.0 μm
 PF: Spherical silica-zirconia (treated with γ-methacryloxypropyltrimethoxysilane),
  Average particle diameter; 0.15 μm The M-value was measured as described below.

Namely, 0.2 g of the sample silica was added to 50 ml of water contained in a beaker of a volume of 250 ml. Next, by using a burette, methanol was added dropwise thereto with stirring by using a magnetic stirrer until the whole amount of silica was suspended and dispersed.

The moment when the whole amount of silica was suspended and dispersed was regarded to be a terminal point, and the volume percentage of methanol in the liquid mixture in the beaker at this moment was regarded to be an M-value.

<(F) Organic Solvents>
 IPA: Isopropyl alcohol
 EtOH: Ethyl alcohol

<Other Components>
 CQ: Camphorquinone
 TPO: 2,4,6-Trimethylbenzoyldiphenylphosphinoxide
 DMBE: Ethyl N,N-dimethyl-p-aminobenzoate
 DEPT: N,N-dihydroxyethyl-p-toluidine <Flexural Strength>

A sample curable composition was prepared by homogeneously mixing the components, put into a mold of 2 mm×2 mm×25 mm, and was cured at 37° C. for one hour to prepare a cured body that served as a test piece. After one hour has passed, the test piece (cured body) was taken out from the mold and was stored in purified water for 24 hours.

The surfaces of the test piece were polished by using a #1500 water-resistant polishing paper. Thereafter, the test piece was fitted onto a universal tester (Autograph manufactured by Shimazu Seisakusho Co.) and was measured for its three-point flexural strength maintaining a distance between the fulcrums of 20 mm and at a crosshead speed of 1 mm/min according to JIS T6514.

<Evaluating the Strength of Adhesion>
Preparation of Mimic Cavity:

Within 24 hours after the slaughter, a bovine foretooth was pulled out, and the enamel surface and the dentin surface were ground by using a #600 emery paper while pouring water so as to be in parallel with the labial face. Next, the compressed air was blown onto the surface that was ground and exposed for about 10 seconds to dry the surface to thereby prepare a model tooth.

A double-sided adhesive tape having a hole of 3 mm in diameter perforated therein was fixed to the surface of the model and, thereafter, a paraffin wax (thickness of 0.5 mm) having a hole of 8 mm in diameter perforated therein was fixed thereto in concentric with the hole of the double-sided tape to form a mimic cavity.

1. Strength of Adhesion of the Chemical Polymerization Curing Type Composite Resin:

A sample curable composition (adhesive) was applied into the mimic cavity, left to stand for 20 seconds and, thereafter, the compressed air was blown thereto for about 10 seconds to dry. A dental chemical polymerization curing type composite resin (Palfique manufactured by Tokuyama Dental Co.) was applied thereon, and was stored at 37° C. for one hour to cure the composite resin to thereby prepare an adhesion test piece.

After dipped in water of 37° C. for 24 hours, the above adhesion test piece was fixed to a stainless steel attachment by using a dental resin cement (Bistite II manufactured by Tokuyama Dental Co.), and was put to a tensile test by using the universal tester (Autograph manufactured by Shimazu Seisakusho Co.) at a crosshead speed of 2 mm/min to measure the strength of tensile adhesion between the enamel or dentin of the tooth and the composite resin.

Four test pieces were prepared for each sample, and were measured for their strengths of tensile adhesion, and an average value thereof was regarded as the strength of adhesion.

2. Strength of Adhesion of the Photopolymerization Curing Type Composite Resin:

A sample curable composition (adhesive) was applied into the mimic cavity, left to stand for 20 seconds and, thereafter, the compressed air was blown thereto for about 10 seconds to dry. Next, the sample adhesive was cured by the irradiation with light from a visible ray irradiator (Power-Light, manufactured by Tokuyama Dental Co.) for 10 seconds. A dental photocurable type composite resin (Palfique Estelite Σ, manufactured by Tokuyama Dental Co.) was applied thereon, and was irradiated with light by using the above visible ray irradiator for 30 seconds to cure the composite resin to thereby prepare an adhesion test piece.

The thus prepared adhesion test piece was measured for its strength of tensile adhesion in quite the same manner as in the above case of using the chemical polymerization curing type composite resin.

3. Strength of Adhesion of the Chemical Polymerization Curing Type Cement Using a Pre-Treating Agent:

A sample curable composition (pre-treating agent) was applied into the mimic cavity, left to stand for 20 seconds and, thereafter, the compressed air was blown thereto for about 10 seconds to dry. Next, by using the chemical polymerization curing type cement that has been kneaded, a metal attachment of SUS304 was adhered and fixed thereto to obtain an adhesion test piece.

The adhesion test piece was stored at 37° C. for 24 hours, and was measured for its strength of tensile adhesion in quite the same manner as in the above testing.

4. Strength of Adhesion of the Chemical Polymerization Curing Type Cement without Pre-Treating Agent:

A sample curable composition (chemical polymerization curing type cement) was applied into the mimic cavity, and onto which a metal attachment of SUS304 was adhered and fixed to obtain an adhesion test piece.

The adhesion test piece was stored at 37° C. for 24 hours, and was measured for its strength of tensile adhesion in quite the same manner as in the above testing.

<Strength of Adhesion after the Thermal Shock Test>

There was provided an adhesion test piece prepared in the same manner as those used for the above-mentioned tests for adhesion strength. The adhesion test piece was put into a thermal shock tester, dipped in a water vessel maintained at 4° C. for one minute, transferred into a water vessel maintained at 60° C. and was dipped therein for one minute, and was returned again into the water vessel maintained at 4° C. The above operation was repeated 3000 times.

The adhesion test piece to which the thermal shocks have been given as described above was measured for its strength of tensile adhesion in quite the same manner as the above test of strength of adhesion.

<Measuring the Amount of Polyvalent Metal Ions>

Of various sample curable compositions, only those mixed solutions (I)-1 to (I)-41 of components to be contained in the packages (I) were prepared, and stirred for 24 hours. Thereafter, the mixed solutions each in an amount of 0.2 g were introduced into 100-ml sample tubes and were diluted to 1% with isopropanol (IPA).

By using an ICP (inductively coupled plasma) emission spectroscopy, the diluted solutions were measured for their Al, La and Ca ion concentrations (mmol/g) per gram of the polymerizable monomer component (A) contained in the packages (I).

By calculating the sum of values obtained by multiplying the ion concentrations by their respective ionic valencies, there was found the amount of ionic bonds, i.e., the amount of polyvalent metal ions/meq per gram of the component (A) contained in the package (I).

The polyvalent metal ions eluted out from the fillers used in Examples and in Comparative Examples were the above-mentioned Al, La and Ca ions only, and no other ions were detected.

<Evaluating the Storage Stability>

The components of the curable composition were contained being divided into two packages (I) and (II). The packages (I) and (II) were stored in an incubator maintained at 37° C. for one month. Thereafter, the components contained in the packages (I) and (II) were mixed together to prepare a sample curable composition. The sample was measured for its various kinds of strength of adhesion (strengths of adhesion after stored at 37° C. for one month) by the above-mentioned methods, and was compared with the strengths of adhesion of the curable composition prepared by mixing the components of the packages (I) and (II) of before being stored at 37° C. to evaluate the storage stability.

Further, the package (I) of the curable composition was stored at 50° C., and the number of days until gelation took place (viscosity has greatly increased to assume a state where there was no fluidity of liquid) was counted by eyes to evaluate the storage stability. The evaluation was conducted every day until one week has passed, and was conducted every week after one week has passed.

<Preparation of the Polyvalent Metal Fillers>

Preparation Example 1

A fluoroaluminosilicate glass powder (Tokuso Ionomer manufactured by Tokuyama Dental Co.) was pulverized into an average particle diameter of 0.5 μm by using a wet continuous-type ball mill (New My-Mill manufactured by Mitsui Kozan Co.). Thereafter, the filler surfaces were treated with 5.0 N hydrochloric acid of an amount of 20 g per gram of the powder for 40 minutes to obtain a polyvalent metal filler (F-1).

0.1 Gram of the thus obtained polyvalent metal filler (F-1) was dipped and held in 10 ml of an aqueous solution containing 10% by weight of maleic acid and maintained at a temperature of 23° C. for 24 hours, and the amount of polyvalent metal ions that have eluted out was analyzed by the ICP (inductively coupled plasma) emission spectroscopy.

As a result, the amount of ions eluted out from the polyvalent metal filler (F-1) in 24 hours was 10 meq/g of filler ($Al^{3+}$=6.7, $La^{3+}$=2.8, $Ca^{2+}$=0.5).

Preparation Example 2

A polyvalent metal filler (F-2) was obtained in quite the same manner as in Preparation Example 1 but conducting the treatment with 5.0 N hydrochloric acid for 20 minutes.

As a result of the ICP emission spectroscopy, the amount of ions eluted out from the polyvalent metal filler (F-2) in 24 hours was 25 meq/g of filler ($Al^{3+}$=16.7, $La^{3+}$=6.9, $Ca^{2+}$=1.4).

Preparation Example 3

A polyvalent metal filler (F-3) was obtained in quite the same manner as in Preparation Example 1 but without at all conducting the treatment with hydrochloric acid.

As a result of the ICP emission spectroscopy, the amount of ions eluted out from the polyvalent metal filler (F-3) in 24 hours was 50 meq/g of filler ($Al^{3+}$=33.4, $La^{3+}$=14.0, $Ca^{2+}$=2.6).

Example 1

The components were mixed together according to the following recipe to prepare a composition (I)-1 which was stored in the package (I).
Component (a-1): PM, 40 g
Component (a-2): Bis-GMA, 24 g
   3G, 16 g
   HEMA, 20 g
Component (D): F-2, 10 g (polyvalent metal ion source)
Component (B): water, 20 g
Component (C): BMOV, 0.1 g (radical generation accelerator)

The components were mixed together according to the following recipe to prepare a composition (II)-1 which was stored in the package (II).
Component (a-2): Bis-GMA, 40 g
   3G, 20 g
   HEMA, 40 g
Component (C): PhBTEOA, 2.5 g (radical-generating species)
   POH, 1 g (radical generation accelerator)

24 Hours after the preparation of the above two packages, the compositions stored in the two packages were mixed together at a weight ratio of 1:1, and the obtained curable composition was measured for its flexural strength.

As a result, the flexural strength was 143.1 MPa.

Examples 2 and 3, Comparative Examples 1 to 3

Curable compositions were prepared and were measured for their flexural strengths in the same manner as in Example 1 but preparing compositions (I)-2 to (I)-6 shown in Table 1 to be stored in the packages (I) instead of the composition (I)-1, preparing compositions (II)-2 to (II)-4 shown in Table 2 to be stored in the packages (II) instead of the composition (II)-1, and mixing them together in combinations shown in Table 3.

The results were as shown in Tables 1 to 3.

Comparative Examples 4 and 5

There were prepared compositions (I)-7 and (I)-8 shown in Table 1 to be stored in the packages (I) instead of the composition (I)-1, and a composition (II)-4 shown in Table 2 to be stored in the package (II) instead of the composition (II)-1. Curable compositions were prepared and were measured for their flexural strengths in the same manner as in Example 1 but mixing them together according to combinations shown in Table 3. However, the compositions (I)-7 and (I)-8 stored in the packages (I) had been cured, and the flexural strengths could not be tested.

TABLE 1

| Composition | A) Polymerizable monomer (g) | | D) Polyvalent metal filler (g) | B) Water (g) | C) Chemical polymerization type polymerization initiator component (g) |
| --- | --- | --- | --- | --- | --- |
| | (a-1) Acidic monomer | (a-2) Non-acidic monomer | | | |
| (I)-1 | PM (40) | Bis-GMA (24)/3G (16)/HEMA (20) | F-2 (10) | 20 | BMOV (0.1) |
| (I)-2 | PM (40) | Bis-GMA (24)/3G (16)/HEMA (20) | F-2 (10) | 20 | BPO (2) |
| (I)-3 | PM (40) | Bis-GMA (24)/3G (16)/HEMA (20) | F-2 (10) | 20 | DEPT (2) |
| (I)-4 | — | Bis-GMA (48)/3G (32)/HEMA (20) | F-2 (10) | 20 | BMOV (0.1) |
| (I)-5 | PM (40) | Bis-GMA (24)/3G (16)/HEMA (20) | — | 20 | BMOV (0.1) |
| (I)-6 | PM (40) | Bis-GMA (24)/3G (16)/HEMA (20) | F-2 (10) | — | BMOV (0.1) |
| (I)-7 | PM (40) | Bis-GMA (24)/3G (16)/HEMA (20) | F-2 (10) | 20 | BMOV (0.1)/PhBTEOA (2.5) |
| (I)-8 | PM (40) | Bis-GMA (24)/3G (16)/HEMA (20) | F-2 (10) | 20 | BPO (2)/DEPT (2) |

TABLE 2

| Composition | A) Polymerizable monomer (g) | C) Chemical polymerization type polymerization initiator component (g) |
| --- | --- | --- |
| (II)-1 | Bis-GMA(40)/3G(20)/HEMA(40) | PhBTEOA(2.5)/POH(1) |
| (II)-2 | Bis-GMA(40)/3G(20)/HEMA(40) | DEPT(2) |
| (II)-3 | Bis-GMA(40)/3G(20)/HEMA(40) | BPO(2) |
| (II)-4 | Bis-GMA(40)/3G(20)/HEMA(40) | — |

TABLE 3

| | Composition | | Flexural strength/Mpa (standard deviation) |
| --- | --- | --- | --- |
| Ex. 1 | (I)-1 | (II)-1 | 143.1(10.3) |
| Ex. 2 | (I)-2 | (II)-2 | 114.5(9.8) |
| Ex. 3 | (I)-3 | (II)-3 | 106.2(8.9) |
| Comp. Ex. 1 | (I)-4 | (II)-1 | 63.4(13.4) |
| Comp. Ex. 2 | (I)-5 | (II)-1 | 13.4(12.1) |
| Comp. Ex. 3 | (I)-6 | (II)-1 | 70.3(15.3) |
| Comp. Ex. 4 | (I)-7 | (II)-4 | * |
| Comp. Ex. 5 | (I)-8 | (II)-4 | ** |

\* (I)-7 was cured and could not be tested
\*\* (I)-8 was cured and could not be tested From the above results, it will be learned that flexural strengths as high as that of Example 1 were obtained in Examples 2 and 3, too.

In Comparative Examples 1 to 3, the flexural strengths were smaller than those of Examples 1 to 3.

Example 4

A composition (I)-9 was prepared according to the following recipe and was stored in the package (I).
Component (a-1): PM, 40 g
Component (a-2): Bis-GMA, 24 g
  3G, 16 g
  HEMA, 20 g
Component (D): F-2, 10 g (polyvalent metal ion source)
Component (B): water, 20 g
Component (C): BMOV, 0.03 g (radical generation accelerator)
Component (E): FS-1, 10 g
Component (F): acetone, 200 g Further, a composition (II)-5 was prepared according to the following recipe and was stored in the package (II).
Component (C): PhBTEOA, 2.5 g (radical-generating species)
Component (F): acetone, 97.5 g 24 Hours after the preparation of the above two packages, the compositions stored in the two packages were mixed together at a weight ratio of 1:1, and the obtained curable composition was measured for its strength of adhesion to the chemical polymerization curing type composite resin, strength of adhesion after the thermal shock test and strength of adhesion after the packages (I) and (II) were stored at 37° C. for one month to evaluate the storage stability. The results were as shown in Table 7.

Examples 5 to 24, Comparative Examples 6 to 8

Compositions were stored in the packages (I) and (II) in the same manner as in Example 4 but preparing compositions (I)-10 to (I)-26 as the compositions to be stored in the packages (I) and preparing compositions (II)-5 to (II)-12 shown in Table 5 as the compositions to be stored in the packages (II).

The compositions stored in the packages (I) and (II) were measured for their strengths of adhesion to the chemical polymerization curing type composite resin, strengths of adhesion after the thermal shock test and strengths of adhesion after the packages (I) and (II) were stored at 37° C. for one month in the same manner as in Example 4. The results were as shown in Table 6.

TABLE 4

| Composition | C)* | E) Inorganic filler (g) | F) Organic solvent (g) | Other component (g) | Amount of ions (meq) |
|---|---|---|---|---|---|
| (I)-9  | BMOV (0.03) | FS-1 (10) | acetone (200) |  | 2.4 |
| (I)-10 | BMOV (0.1)  | FS-1 (10) | acetone (200) |  | 2.4 |
| (I)-11 | BMOV (0.2)  | FS-1 (10) | acetone (200) |  | 2.5 |
| (I)-12 | BMOV (0.1)  | FS-1 (3)  | acetone (200) |  | 2.4 |
| (I)-13 | BMOV (0.1)  | FS-1 (20) | acetone (200) |  | 2.4 |
| (I)-14 | BMOV (0.1)  | FS-2 (10) | acetone (200) |  | 2.4 |
| (I)-15 | BMOV (0.1)  | MS (10)   | acetone (200) |  | 2.4 |
| (I)-16 | BMOV (0.1)  | SS (10)   | acetone (200) |  | 2.4 |
| (I)-17 | BMOV (0.1)  | FS-1 (10) | acetone (50)  |  | 2.4 |
| (I)-18 | BMOV (0.1)  | FS-1 (10) | acetone (300) |  | 2.4 |
| (I)-19 | BMOV (0.1)  | FS-1 (10) | IPA (200)     |  | 2.4 |
| (I)-20 | BMOV (0.1)  | FS-1 (10) | EtOH (200)    |  | 2.4 |
| (I)-21 | BMOV (0.1)  | FS-1 (10) | acetone (200) | CQ (0.5) | 2.4 |
| (I)-22 | BMOV (0.1)  | FS-1 (10) | acetone (200) | TPO (0.5) | 2.4 |
| (I)-23 | BMOV (0.1)  | FS-1 (10) | acetone (200) | CQ (0.5)/TPO (0.5) | 2.4 |
| (I)-24 | —           | FS-1 (10) | acetone (200) | CQ (0.5)/TPO (0.5) | 2.4 |
| (I)-25 | BMOV (0.1)/PhBTEOA (2) | FS-1(10) | acetone (200) |  | 2.4 |
| (I)-26 | BMOV (0.1)/POH (2)     | FS-1 (10) | acetone (200) |  | 2.4 |

*C) Chemical polymerization type polymerization initiator component (g)

Note:

Each composition contained 40 g of PM, 24 g of bis-GMA, 16 g of 3G and 20 g of HEMA as the component (A), 10 g of F-2 as the component (D) and 20 g of water as the component (B) in addition to the above composition.

TABLE 5

| Composition | A) Polymerizable monomer (g) | C) Chemical polymerization type polymerization initiator component (g) | F) Organic solvent (g) | Others (g) |
|---|---|---|---|---|
| (II)-5  | —                        | PhBTEOA(2.5)       | acetone(97.5) | — |
| (II)-6  | —                        | PhBTEOA(2.5)/POH(1) | acetone(96.5) | — |
| (II)-7  | —                        | PhBTEOA(2.5)       | acetone(96.5) | DMBE(1) |
| (II)-8  | Bis-GMA(30)/3G(20)       | PhBTEOA(2.5)       | acetone(47.5) | — |
| (II)-9  | —                        | PhBTEOA(2.5)/POH(1) | acetone(95.5) | DMBE(1) |
| (II)-10 | —                        | —                  | acetone(100)  | — |
| (II)-11 | —                        | PhBTEOA(2.5)       | acetone(87.5) | F-2(10) |
| (II)-12 | Bis-GMA(40)/3G(20)/HEMA(40) | PhBTEOA(2.5)    | —             | — |

TABLE 6

| | Composition | | Strength of adhesion/MPa (standard deviation) | | Strength of adhesion after thermal shock/MPa (standard deviation) | | Strength of adhesion after packages (I), (II) were stored at 37° C. for a month/MPa (standard deviation) | |
|---|---|---|---|---|---|---|---|---|
| | | | enamel | dentin | enamel | dentin | enamel | dentin |
| Ex. 4 | (I)-9 | (II)-6 | 18.9 (3.4) | 19.5 (2.2) | 18.1 (2.3) | 17.1 (4.2) | 18.9 (2.8) | 19.1 (3.8) |
| Ex. 5 | (I)-10 | (II)-6 | 22.1 (3.2) | 20.2 (2.2) | 21.3 (3.5) | 22.6 (4.5) | 21.4 (3.8) | 19.5 (3.2) |
| Ex. 6 | (I)-11 | (II)-6 | 21.1 (4.3) | 21.5 (3.8) | 21.4 (3.1) | 22.4 (4.9) | 20.9 (3.3) | 20.4 (4.2) |
| Ex. 7 | (I)-12 | (II)-6 | 19.4 (4.8) | 18.7 (2.9) | 16.4 (4.4) | 15.6 (5.4) | 18.7 (3.5) | 17.9 (4.2) |
| Ex. 8 | (I)-13 | (II)-6 | 17.8 (3.4) | 19.4 (3.4) | 18.4 (5.6) | 16.6 (3.4) | 17.4 (2.9) | 18.9 (5.4) |
| Ex. 9 | (I)-14 | (II)-6 | 24.2 (3.2) | 22.1 (4.1) | 22.5 (2.1) | 23.1 (2.6) | 20.9 (3.8) | 21.5 (1.6) |
| Ex. 10 | (I)-15 | (II)-6 | 15.9 (3.4) | 17.9 (3.3) | 19.4 (4.4) | 17.3 (3.1) | 15.8 (2.9) | 17.3 (2.6) |
| Ex. 11 | (I)-16 | (II)-6 | 16.9 (3.9) | 16.9 (4.4) | 15.3 (3.7) | 16.2 (2.1) | 16.4 (3.7) | 16.2 (3.7) |
| Ex. 12 | (I)-17 | (II)-6 | 18.3 (5.3) | 16.5 (3.1) | 16.3 (3.4) | 15.1 (3.6) | 14.8 (3.4) | 13.9 (4.4) |
| Ex. 13 | (I)-18 | (II)-6 | 17.8 (3.3) | 18.2 (4.1) | 15.4 (4.5) | 15.8 (3.5) | 17.5 (2.2) | 17.8 (4.2) |
| Ex. 14 | (I)-19 | (II)-6 | 20.0 (2.4) | 21.4 (3.2) | 19.5 (3.4) | 18.2 (3.1) | 18.9 (3.2) | 18.1 (3.8) |
| Ex. 15 | (I)-20 | (II)-6 | 21.9 (4.2) | 22.2 (4.2) | 19.1 (3.4) | 20.5 (3.4) | 19.1 (3.3) | 20.2 (1.9) |
| Ex. 16 | (I)-21 | (II)-6 | 20.4 (4.1) | 21.6 (2.8) | 20.1 (5.1) | 20.8 (4.7) | 19.7 (3.1) | 20.4 (2.9) |
| Ex. 17 | (I)-22 | (II)-6 | 20.4 (1.2) | 21.1 (4.3) | 20.2 (2.9) | 20.8 (3.8) | 20.1 (3.9) | 19.9 (3.3) |
| Ex. 18 | (I)-23 | (II)-6 | 19.9 (3.2) | 19.5 (2.2) | 20.9 (4.3) | 19.3 (4.1) | 18.9 (3.5) | 20.4 (4.5) |
| Ex. 19 | (I)-24 | (II)-6 | 10.3 (5.2) | 12.1 (3.9) | 10.4 (5.2) | 10.5 (4.2) | 10.1 (5.5) | 11.9 (3.8) |
| Ex. 20 | (I)-10 | (II)-5 | 11.5 (3.4) | 12.8 (4.5) | 10.4 (2.1) | 10.3 (5.9) | 10.9 (3.1) | 12.3 (4.9) |
| Ex. 21 | (I)-10 | (II)-7 | 14.3 (5.3) | 13.8 (3.9) | 12.1 (4.4) | 13.1 (3.6) | 13.4 (4.3) | 14.4 (4.4) |
| Ex. 22 | (I)-10 | (II)-8 | 13.4 (4.8) | 13.1 (5.1) | 14.5 (5.7) | 11.4 (3.4) | 12.5 (4.3) | 13.0 (4.2) |
| Ex. 23 | (I)-10 | (II)-11 | 13.6 (2.8) | 14.2 (4.2) | 13.5 (4.2) | 13.6 (3.6) | 11.5 (2.8) | 12.2 (3.8) |
| Ex. 24 | (I)-10 | (II)-12 | 13.2 (2.1) | 14.3 (3.9) | 12.5 (4.3) | 11.4 (3.8) | 13.1 (3.6) | 13.6 (4.3) |
| Comp. Ex. 6 | (I)-25 | (II)-6 | * | * | * | * | * | * |
| Comp. Ex. 7 | (I)-26 | (II)-6 | * | * | * | * | * | * |
| Comp. Ex. 8 | (I)-10 | (II)-10 | 0.0 (0.0) | 2.3 (1.1) | 1.1 (0.4) | 1.4 (1.1) | 0.0 (0.0) | 2.1 (1.9) |

* cured at the time of use and could not be tested

In Examples 4 to 24, the components were so blended as to satisfy the constitution of the invention, and favorable strengths of adhesion were obtained to both the enamel and the dentin. There were, further, obtained large strengths of adhesion even after the thermal shock test and large strengths of adhesion to the tooth even after the packages (I) and (II) were stored at 37° C. for one month.

In Comparative Examples 6 and 7, on the other hand, the chemical polymerization initiator component (C) was all contained in the package (I). After the passage of 24 hours, however, the compositions had been cured and could not be tested.

In Comparative Example 8, the chemical polymerization initiator component (C), i.e., the aryl borate compound (radical-generating species) was not contained in the package (II). In this case, the strength of adhesion of the curable composition was very low, and a sufficiently large curing property was not obtained.

Example 25

A composition (I)-27 was prepared according to the following recipe and was stored in the package (I).
Component (a-1): PM, 20 g
Component (a-2): Bis-GMA, 30 g
  3G, 20 g
  HEMA, 30 g
Component (D): F-2, 10 g (polyvalent metal ion source)
Component (B): water, 20 g
Component (C): BMOV, 0.1 g (radical generation accelerator)
Component (E): FS-1, 10 g
Component (F): acetone, 10 g Further, a composition (II)-6 was prepared according to the following recipe and was stored in the package (II).
Component (C) PhBTEOA, 2.5 g (radical-generating species)
  POH, 1 g (radical generation accelerator)
Component (F): acetone, 96.5 g 24 Hours after the preparation of the above two packages, the compositions stored in the two packages were mixed together at a weight ratio of 1:1, and the obtained curable composition was measured for its strength of adhesion to the chemical polymerization curing type composite resin, strength of adhesion after the thermal shock test, strength of adhesion after the packages (I) and (II) were stored at 37° C. for one month, and the number of days until the gelation occurred when the package (I) was stored at 50° C. The results were as shown in Table 8.

Examples 26 to 45, Comparative Examples 9 to 12

Compositions (I)-28 to (I)-44 were prepared according to the recipe shown in Table 7 and were stored in the packages (I) in the same manner as in Example 25.

Further, a composition (II)-6 shown in Table 5 was prepared and stored in the package (II).

24 Hours after the preparation of the above two kinds of packages, the compositions stored in the two packages were mixed together at a weight ratio of 1:1, and the obtained curable compositions was measured for their strengths of adhesion to the chemical polymerization curing type composite resin, strengths of adhesion after the thermal shock test, strengths of adhesion after the packages (I) and (II) were stored at 37° C. for one month, and the number of days until the gelation occurred when the packages (I) was stored at 50° C. The results were as shown in Table 8.

TABLE 7

| Composition | A) Polymerizable monomer (g) (a-1) Acidic monomer | A) Polymerizable monomer (g) (a-2) Non-acidic monomer | D) Polyvalent metal filler (g) | B) Water (g) | Amount of ions (meq) |
|---|---|---|---|---|---|
| (I)-27 | PM (20) | Bis-GMA (30)/3G (20)/HEMA (30) | F-2 (10) | 20 | 2.4 |
| (I)-28 | PM (60) | Bis-GMA (20)/3G (10)/HEMA (10) | F-2 (10) | 20 | 2.4 |
| (I)-29 | PM (80) | Bis-GMA (6)/3G (4)/HEMA (10) | F-2 (10) | 20 | 2.4 |
| (I)-30 | PM (100) | — | F-2 (10) | 20 | 2.4 |
| (I)-31 | MDP (40) | Bis-GMA (24)/3G (16)/HEMA (20) | F-2 (10) | 20 | 2.4 |
| (I)-32 | MAC10 (40) | Bis-GMA (24)/3G (16)/HEMA (20) | F-2 (10) | 20 | 2.4 |
| (I)-33 | PM (40) | Bis-GMA (24)/3G (16)/HEMA (20) | F-2 (6) | 20 | 1.4 |
| (I)-34 | PM (40) | Bis-GMA (24)/3G (16)/HEMA (20) | F-2 (20) | 20 | 4.8 |
| (I)-35 | PM (40) | Bis-GMA (24)/3G (16)/HEMA (20) | F-1 (10) | 20 | 1.0 |
| (I)-36 | PM (40) | Bis-GMA (24)/3G (16)/HEMA (20) | F-1 (7) | 20 | 0.7 |
| (I)-37 | PM (40) | Bis-GMA (24)/3G (16)/HEMA (20) | F-1 (5) | 20 | 0.5 |
| (I)-38 | PM (20) | Bis-GMA (30)/3G (20)/HEMA (30) | F-1 (7) | 20 | 0.7 |
| (I)-39 | PM (80) | Bis-GMA (6)/3G (4)/HEMA (10) | F-1 (7) | 20 | 0.7 |
| (I)-40 | MDP (40) | Bis-GMA (24)/3G (16)/HEMA (20) | F-1 (7) | 20 | 0.7 |
| (I)-41 | MAC10 (40) | Bis-GMA (24)/3G (16)/HEMA (20) | F-1 (7) | 20 | 0.7 |
| (I)-42 | PM (40) | Bis-GMA (24)/3G (16)/HEMA (20) | F-1 (7) | 10 | 0.7 |
| (I)-43 | PM (40) | Bis-GMA (24)/3G (16)/HEMA (20) | F-1 (7) | 30 | 0.7 |
| (I)-44 | PM (40) | Bis-GMA (24)/3G (16)/HEMA (20) | F-3 (10) | 20 | 4.8 |
| (I)-45 | PM (40) | Bis-GMA (24)/3G (16)/HEMA (20) | F-3 (18) | 20 | 8 |
| (I)-46 | PM (40) | Bis-GMA (24)/3G (16)/HEMA (20) | F-2 (10) | 10 | 2.4 |
| (I)-47 | PM (40) | Bis-GMA (24)/3G (16)/HEMA (20) | F-2 (10) | 30 | 2.4 |
| (I)-48 | — | Bis-GMA (40)/3G (30)/HEMA (30) | F-2 (10) | 20 | 0 |
| (I)-49 | PM (40) | Bis-GMA (24)/3G (16)/HEMA (20) | — | 20 | 0 |
| (I)-50 | PM (40) | Bis-GMA (24)/3G (16)/HEMA (20) | F-3 (25) | 20 | 12 |
| (I)-51 | PM (40) | Bis-GMA (24)/3G (16)/HEMA (20) | F-2 (10) | — | 0 |

*Each composition contained 0.1 g of BMOV as the component (D), 10 g of FS-1 as the component (E) and 100 g of acetone as the component (F) in addition to the above composition.

TABLE 8

| | Composition | | Strength of adhesion/MPa (standard deviation) enamel | Strength of adhesion/MPa (standard deviation) dentin | Strength of adhesion after thermal shock/MPa (standard deviation) enamel | Strength of adhesion after thermal shock/MPa (standard deviation) dentin | Strength of adhesion after packages (I), (II) were stored at 37° C. for a month/MPa (standard deviation) enamel | Strength of adhesion after packages (I), (II) were stored at 37° C. for a month/MPa (standard deviation) dentin | * |
|---|---|---|---|---|---|---|---|---|---|
| Ex. 25 | (I)-27 | (II)-6 | 20.3 (4.0) | 20.5 (3.1) | 19.3 (3.2) | 20.8 (4.1) | 19.2 (3.5) | 19.7 (3.2) | 21 days |
| Ex. 26 | (I)-28 | (II)-6 | 21.3 (6.3) | 17.9 (5.2) | 17.9 (4.3) | 16.4 (3.5) | 20.4 (5.3) | 17.4 (4.2) | 21 days |
| Ex. 27 | (I)-29 | (II)-6 | 16.4 (3.6) | 13.7 (2.4) | 11.4 (5.3) | 12.6 (3.5) | 16.3 (3.2) | 13.3 (3.4) | 21 days |
| Ex. 28 | (I)-30 | (II)-6 | 13.2 (1.4) | 11.3 (4.9) | 10.8 (5.3) | 10.4 (4.9) | 12.9 (3.1) | 11.1 (4.3) | 21 days |
| Ex. 29 | (I)-31 | (II)-6 | 15.4 (3.4) | 13.4 (3.4) | 14.5 (5.3) | 14.3 (4.7) | 14.4 (4.3) | 13.1 (4.3) | 21 days |
| Ex. 30 | (I)-32 | (II)-6 | 13.4 (5.3) | 13.1 (2.3) | 13.2 (3.4) | 12.8 (2.8) | 12.6 (3.2) | 12.6 (2.9) | 21 days |
| Ex. 31 | (I)-33 | (II)-6 | 16.8 (4.3) | 15.8 (4.2) | 14.9 (5.4) | 16.3 (3.2) | 15.9 (3.1) | 15.4 (2.7) | 42 days |
| Ex. 32 | (I)-34 | (II)-6 | 24.4 (2.4) | 23.1 (3.6) | 22.4 (4.8) | 22.7 (5.3) | 18.4 (2.7) | 17.3 (4.2) | 7 days |
| Ex. 33 | (I)-35 | (II)-6 | 18.5 (3.1) | 16.9 (3.5) | 17.4 (3.6) | 16.4 (4.3) | 18.1 (3.9) | 16.3 (4.1) | 56 days |
| Ex. 34 | (I)-36 | (II)-6 | 16.2 (4.4) | 15.8 (3.3) | 15.6 (4.1) | 15.2 (3.6) | 16.3 (3.8) | 15.9 (2.1) | 56 days |
| Ex. 35 | (I)-37 | (II)-6 | 11.8 (3.5) | 12.2 (3.1) | 11.6 (3.1) | 11.4 (4.6) | 11.9 (4.5) | 11.5 (2.2) | 56 days |
| Ex. 36 | (I)-38 | (II)-6 | 15.8 (3.8) | 16.1 (4.2) | 15.5 (3.3) | 15.1 (4.3) | 15.5 (5.2) | 16.1 (3.6) | 56 days |
| Ex. 37 | (I)-39 | (II)-6 | 12.4 (3.5) | 12.6 (2.9) | 11.9 (4.6) | 11.5 (4.8) | 12.0 (1.8) | 12.1 (4.4) | 56 days |
| Ex. 38 | (I)-40 | (II)-6 | 11.8 (4.4) | 11.3 (3.9) | 10.9 (5.1) | 10.7 (3.8) | 11.5 (4.7) | 11.0 (3.8) | 56 days |
| Ex. 39 | (I)-41 | (II)-6 | 11.5 (3.2) | 11.1 (2.9) | 10.1 (2.9) | 10.3 (3.1) | 10.9 (3.4) | 10.8 (2.6) | 56 days |
| Ex. 40 | (I)-42 | (II)-6 | 15.9 (4.4) | 15.2 (5.1) | 14.3 (2.2) | 14.1 (3.9) | 14.8 (2.8) | 14.5 (4.4) | 56 days |
| Ex. 41 | (I)-43 | (II)-6 | 14.5 (2.9) | 14.1 (2.8) | 12.9 (3.7) | 12.5 (3.3) | 13.6 (3.8) | 13.4 (3.2) | 56 days |
| Ex. 42 | (I)-44 | (II)-6 | 21.4 (4.3) | 22.6 (3.8) | 21.6 (3.5) | 20.3 (2.9) | 16.9 (5.3) | 15.8 (3.1) | 7 days |
| Ex. 43 | (I)-45 | (II)-6 | 18.5 (5.6) | 19.5 (3.3) | 17.8 (4.3) | 18.4 (3.5) | 13.3 (5.4) | 15.9 (4.3) | 3 days |
| Ex. 44 | (I)-46 | (II)-6 | 16.8 (4.3) | 18.4 (3.4) | 17.4 (3.5) | 16.8 (4.1) | 16.4 (3.2) | 17.7 (3.2) | 21 days |
| Ex. 45 | (I)-47 | (II)-6 | 17.4 (3.6) | 17.3 (4.3) | 14.5 (4.2) | 15.7 (3.2) | 16.9 (3.7) | 17.2 (4.1) | 21 days |
| Comp. Ex. 9 | (I)-48 | (II)-6 | 3.2 (1.0) | 2.1 (2.5) | 0.0 (0.0) | 0.4 (0.2) | 2.2 (2.1) | 1.6 (0.9) | 21 days |
| Comp. Ex. 10 | (I)-49 | (II)-6 | 5.8 (5.3) | 6.3 (4.2) | 4.3 (2.9) | 5.4 (3.2) | 5.3 (3.7) | 5.5 (3.9) | 56 days |
| Comp. Ex. 11 | (I)-50 | (II)-6 | 9.9 (1.2) | 8.8 (3.4) | 8.3 (2.6) | 8.5 (2.8) | gelled | gelled | one day |
| Comp. Ex. 12 | (I)-51 | (II)-6 | 6.9 (3.2) | 7.9 (3.1) | 4.1 (0.9) | 2.9 (2.1) | 5.3 (4.4) | 7.2 (3.4) | 56 days |

* Number of days until gelation occurs when package (I) is stored at 50° C.

In Examples 25 to 45, the components were so blended as to satisfy the constitution of the invention, and favorable strengths of adhesion were obtained to both the enamel and the dentin. There were, further, obtained large strengths of adhesion even after the thermal shock test and large strengths of adhesion to the tooth even after the packages (I) and (II) were stored at 37° C. for one month. Even when the package (I) was stored at 50° C., further, the gelation occurred only after the passage of an extended period of time and favorable storage stability was obtained.

Comparative Examples 9, 10 and 12, on the other hand, contained neither the component (a-1), i.e., acidic monomer nor the component (B), i.e., water which are essential for the present invention. Besides, no polyvalent metal ion was introduced into the composition in the package (I). Therefore, large strengths of adhesion were not obtained. In Comparative Example 11, further, polyvalent metal ions were blended in an excess amount causing, therefore, a decrease in the tooth-demineralizing power. Therefore, a large strength of adhesion was not obtained. Besides, the gelation occurred in 20 days when the packages (I) and (II) were stored at 37° C., and occurred in one day when the package (I) was stored at 50° C.

Examples 46 to 49

The compositions (I)-21 to (I)-24 shown in Table 4 were stored in the packages (I), respectively, and the compositions (II)-6 and (II)-9 shown in Table 5 were stored in the packages (II), respectively.

24 Hours after the preparation of the above two kinds of packages, the compositions stored in these two kinds of packages were mixed together in combinations shown in Table 9 and at a weight ratio of 1:1, and the obtained curable compositions were measured for their strengths of adhesion to the photopolymerization curing type composite resin, strengths of adhesion after the thermal shock test, and strengths of adhesion after the packages (I) and (II) were stored at 37° C. for one month. The results were as shown in Table 9.

TABLE 9

| | Composition | | Strength of adhesion/MPa (standard deviation) | | Strength of adhesion after thermal shock/MPa (standard deviation) | | Strength of adhesion after packages (I), (II) were stored at 37° C. for a month/MPa (standard deviation) | |
|---|---|---|---|---|---|---|---|---|
| | | | enamel | dentin | enamel | dentin | enamel | dentin |
| Ex. 46 | (I)-21 | (II)-9 | 20.4 (5.3) | 21.1 (1.8) | 21.4 (3.1) | 20.1 (2.4) | 19.3 (3.5) | 19.8 (2.9) |
| Ex. 47 | (I)-22 | (II)-6 | 18.5 (3.2) | 19.4 (3.1) | 19.8 (3.7) | 20.4 (4.3) | 17.6 (2.2) | 19.2 (4.3) |
| Ex. 48 | (I)-23 | (II)-9 | 20.8 (4.2) | 21.3 (5.3) | 18.9 (3.7) | 17.5 (3.8) | 19.9 (3.2) | 18.9 (4.2) |
| Ex. 49 | (I)-24 | (II)-9 | 21.2 (3.8) | 20.6 (2.8) | 20.4 (3.4) | 20.7 (2.8) | 19.6 (3.7) | 18.4 (3.8) |

Example 50

Preparation of a Cement Composition

A matrix for cement was prepared by adding, as a reaction species of chemical polymerization initiator, 2 g of DEPT which is a tertiary amine to 100 g of a mixture of polymerizable monomers comprising 60 g of bis-GMA and 40 g of 3G. To the matrix, there were added 200 g of GF as the inorganic filler and 120 g of PF, which were mixed together at a dark place in an agate mortar until a homogeneously mixed composition was obtained to thereby prepare a cement composition (CRA-1).

Further, a matrix was prepared by adding, as a reaction species of chemical polymerization initiator, 2 g of BPO which is an organic peroxide to 100 g of a mixture of polymerizable monomers comprising 60 g of bis-GMA and 40 g of 3G. To the matrix, there were added 200 g of GF as the inorganic filler and 120 g of PF, which were mixed together at a dark place in an agate mortar until a homogeneously mixed composition was obtained to thereby prepare a cement composition (CRB-1).

(Preparation of a Pre-Treating Agent)

The above composition (I)-10 was put into the package (I) and the composition (II)-6 was put into the package (II). After these packages were stored for 24 hours, the components contained in these packages were mixed together at a weight ratio of 1:1 to prepare a curable composition for use as a pre-treating agent.

(Evaluating the Strengths of Adhesion)

The cement compositions (CRA-1) and (CRB-1) prepared above were mixed together to prepare a chemical polymerization curing type cement.

By using the above curable composition as a pre-treating agent, the chemical polymerization curing type cement prepared above was measured for its strength of adhesion (see Evaluation 3 of strengths of adhesion). The strength of adhesion after the thermal shock test was also measured. The results were as follows:

Strength of adhesion to the enamel: 21.5(3.2) MPa
Strength of adhesion to the dentin: 22.3(4.6) MPa
Strengths of adhesion after the thermal shock test:
To the enamel: 20.6(2.9) MPa
To the dentin: 23.4(4.1) MPa Example 51

A composition (SAA-1) for package (I) was prepared according to the following recipe and was stored in the package (I).

Component (a-1): PM, 25 g
Component (a-2): Bis-GMA, 20 g
3G, 45 g
HEMA, 10 g
Component (D): F-2, 10 g
Component (B): water, 10 g
Component (C): BMOV, 0.1 g (radical generation accelerator)
Component (E): MS, 200 g Further, a composition (SAB-1) for package (II) was prepared according to the following recipe and was stored in the package (II).

Component (a-2): Bis-GMA, 30 g
3G, 70 g
Component (C): PhBTEOA, 2.5 g (radical-generating species)
POH, 2 g (radical generation accelerator)
Component (E): MS, 200 g The composition (CRA-1) stored in the package (I) and the composition (CRB-1) stored in the package (II) were mixed together to prepare a curable composition.

By using the curable composition as a chemical polymerization curing type cement, the chemical polymerization curing type cement without the pre-treating agent was measured for its strength of adhesion (see Evaluation 4 of strengths of adhesion). The strength of adhesion after the thermal shock test was also measured. The results were as follows:

Strength of adhesion to the enamel: 17.8(7.3) MPa
Strength of adhesion to the dentin: 10.1(5.4) MPa
Strengths of adhesion after the thermal shock test:
    To the enamel: 15.6(3.8) MPa
    To the dentin: 9.4(3.1) MPa

The invention claimed is:

1. A dental curable composition including:
(A) a polymerizable monomer component containing an acidic group-containing polymerizable monomer;
(B) water; and
(C) a chemical polymerization initiator component comprising a radical-generating species and a reactive species that generates radicals upon reacting with the radical-generating species; wherein,
    said dental curable composition is stored being divided into a plurality of packages, and is polymerized and cured by mixing together components contained in the packages; and wherein,
    one package (I) among said packages contains said component (A) and said component (B), and, further, contains polyvalent metal ions in an amount of 0.3 to 10 meq per gram of the polymerizable monomer component (A) contained in said package, wherein the acidic group-containing polymerizable monomer is conically crosslinked;
    said polyvalent metal ions is at least one selected from the group consisting of aluminum ions, lanthanum ions, and titanium ions; and
    said chemical polymerization initiator (C) is stored being divided into at least two packages so that the radical-generating species and the reactive species do not come in contact with each other.

2. The dental curable composition according to claim 1, wherein said acidic group-containing polymerizable monomer is contained in a whole amount in said package (I).

3. The dental curable composition according to claim 1, wherein said radical-generating species is an aryl borate compound, said reactive species is an acidic compound, and said aryl borate compound is stored in a package that does not contain said acidic group-containing polymerizable monomer.

4. The dental curable composition according to claim 3, wherein a radical generation accelerator is contained as said chemical polymerization initiator component (C) in any one of the packages, said radical generation accelerator being at least one selected from a vanadium compound having a valency of +IV or +V and an organoperoxide.

5. The dental curable composition according to claim 4, wherein said vanadium compound having a valency of +IV or +V is contained in said package (I).

6. The dental curable composition according to claim 4, wherein said organoperoxide is contained in a package separate from said package (I) and the package containing said acidic compound.

7. The dental curable composition according to claim 1, wherein (D) a polyvalent metal ion source is further contained, and a polyvalent metal ion-eluting filler is contained as said polyvalent metal ion source in said package (I).

8. The dental curable composition according to claim 7, wherein the polyvalent metal ion-eluting filler is a fluoroaluminosilicate glass.

9. The dental curable composition according to claim 1, wherein an amount of water (B) contained in said package (I) is 3 to 30 parts by mass per 100 parts by mass of the polymerizable monomer component (A) in said package (I).

10. The dental curable composition according to claim 1, wherein (E) a polyvalent metal ion non-eluting inorganic filler is contained in any one of the packages.

11. The dental curable composition according to claim 10, wherein said polyvalent metal ion non-eluting inorganic filler is a fumed silica.

12. The dental curable composition according to claim 1, wherein said package (I) contains a volatile water-soluble organic solvent (F).

13. A dental adhesive comprising the dental curable composition according to claim 1.

* * * * *